US009753018B2

(12) United States Patent
Yamashita et al.

(10) Patent No.: US 9,753,018 B2
(45) Date of Patent: Sep. 5, 2017

(54) SELENIUM-CONTAINING COMPOUND

(71) Applicant: Fisheries Research Agency, Yokohama-shi, Kanagawa (JP)

(72) Inventors: Yumiko Yamashita, Yokohama (JP); Michiaki Yamashita, Yokohama (JP); Takeshi Yabu, Yokohama (JP)

(73) Assignee: Fisheries Research Agency, Yokohama (JP)

( * ) Notice: Subject to any disclaimer, the term of this patent is extended or adjusted under 35 U.S.C. 154(b) by 0 days.

(21) Appl. No.: 15/158,026

(22) Filed: May 18, 2016

(65) Prior Publication Data

US 2016/0266079 A1 Sep. 15, 2016

Related U.S. Application Data

(63) Continuation of application No. 14/754,632, filed on Jun. 29, 2015, now Pat. No. 9,393,231, which is a continuation of application No. 12/948,028, filed on Nov. 17, 2010, now Pat. No. 9,109,158.

(30) Foreign Application Priority Data

Dec. 11, 2009 (JP) ................................ 2009-282034

(51) Int. Cl.
| C09K 15/00 | (2006.01) |
| G01N 30/72 | (2006.01) |
| A61K 8/58 | (2006.01) |
| A61Q 19/08 | (2006.01) |
| C07D 233/66 | (2006.01) |
| C09K 15/32 | (2006.01) |
| A61K 31/4164 | (2006.01) |
| A61K 31/4178 | (2006.01) |
| A23L 33/10 | (2016.01) |
| A23L 33/16 | (2016.01) |

(52) U.S. Cl.
CPC ......... *G01N 30/7233* (2013.01); *A23L 33/10* (2016.08); *A23L 33/16* (2016.08); *A61K 8/58* (2013.01); *A61K 31/4164* (2013.01); *A61K 31/4178* (2013.01); *A61Q 19/08* (2013.01); *C07D 233/66* (2013.01); *C09K 15/328* (2013.01); *A61K 2800/522* (2013.01)

(58) Field of Classification Search
None
See application file for complete search history.

(56) References Cited

U.S. PATENT DOCUMENTS

2007/0244175 A1* 10/2007 Beelman ............. C07D 233/02
514/401

FOREIGN PATENT DOCUMENTS

JP 2001-231498 A 8/2001

OTHER PUBLICATIONS

Arima et al., "Mercury and Selenium Content of *Odontoceti*," *Bulletin of the Japanese Society of Scientific Fisheries*, 45(5): 623-626 (1979).
Assmann et. al., "One-Electron Reduction of Selenomethionine Oxide," *Free Rad. Res.*, 32: 371-376 (2000).
Caroli et al., "The Determination of Chemical Elements in Food: Applications for Atomic and Mass Spectroscopy," National Institute of Health, Wiley-Interscience, Chapter 19 (2007).
Chemical Abstracts, entry for U.S. Patent Application Publication 2007/0244175 (STN; Chemical Abstracts Service: Columbus, OH, 2013; RN 949141-26-8 added to STN Oct. 4, 2007; accessed Oct. 9, 2013).
Combs Jr. et al., "The Role of Selenium in Nutrition," Academic Press, pp. 1-525 (1986).
Combs Jr. et al., "Selenium in Global Food Systems," *British Journal of Nutrition*, 85(5): 517-547 (2001).
Edmonds et al., "The Identification of Selenium Species in Biological Samples," *Appl. Organometal. Chem.*, 14: 133-145 (2000).
El-Ba Youmy et al., "The Protective Role of Selenium on Genetic Damage and on Cancer," *Mutation Research*, 475: 123-139 (2001).
Ge et al., "Identification of Selenium Species in Selenium-enriched Garlic, Onion and Broccoli Using High-Performance Ion Chromatography with Inductively Coupled Plasma Mass Spectrometry Detection," *Analytical Communications*, 33: 279-281 (1996).
Ghose et al., "Selenium and Signal Transduction: Roads to Cell Death and Anti-Tumour Activity," *BioFactors*, 14: 127-133 (2001).
Himeno, "Selenium—Nutrition of Minerals/Trace Elements," edited by Tsugumi Suzuki and Osamu Wada, Daiichi Shuppan Co., Ltd., pp. 423-445 (1994).
Kawakami, "Vitamin E and Respiratory Diseases," *Clinician*, 356: 63-66 (1986).
Kiremidjian-Schumacher et al., "Effect of Selenium on the Immunocompetence of Patients with Head and Neck Cancer and on Adoptive Immunotherapy of Early and Established Lesions," *BioFactors*, 14: 161-168 (2001).
Ministry of Health, Labour and Welfare, "Dietary Reference Intakes for Japanese," pp. 8-47 (Nov. 22, 2004).
(Continued)

*Primary Examiner* — Jeanette Lieb
(74) *Attorney, Agent, or Firm* — Leydig, Voit & Mayer, Ltd.

(57) ABSTRACT

The invention provides a method of improving an antioxidant effect in a redox pathway that involves selenium in a subject, an in vitro method of inhibiting oxidation in a cell or tissue, and an in vitro method of promoting proliferation of a cell, by use of a selenium-containing compound of chemical formula 1:

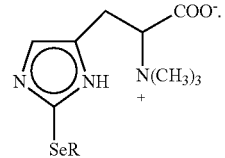

Chemical formula 1

6 Claims, 14 Drawing Sheets

(56) References Cited

OTHER PUBLICATIONS

National Institute of Technology and Evaluation, "Selenium and its Compounds," Chemical Management Center, Ver. 0.4, No. 128, Item 1-178 (2006).
Salonen et al., "Association between Cardiovascular Death and Myocardial Infarction and Serum Selenium in a Matched-Pair Longitudinal Study," *The Lancet,* 2: 175-179 (1982).
Suzuki, Yasuo (editor), "Table of Trace Element Contents in Japanese Food Stuffs," Daiichi Shuppan Co., Ltd., pp. 1-169 (1993).
Watkinson et al., "Fluorometric Determination of Selenium in Biological Material with 2,3-Diaminonaphthalene," *Analytical Chemistry,* 38(1): 92-97 (1966).
Yamashita et al., "Purification and structure determination of novel selenium compound contained in tuna dark muscle," Study Session sponsored by the National Research Institute of Fisheries Sciences of the Fisheries Research Agency of Japan, pp. 122-123, presentation 2-23 (Nov. 18, 2009).
Yamashita et al., "Food Chemical Research on Essential Trace Elements in Fish," Marine Product Processing Research Result/Program Summary (1993), National Research Institute of Fisheries Science, Fisheries Agency, pp. 10-11 (Feb. 1994).
Yamashita et al., "Food Chemical Research on Essential Trace Elements in Fish," Marine Product Processing Research Result/Program Summary (1996), National Research Institute of Fisheries Science, Fisheries Agency, pp. 28-29 (Feb. 1997).
Pending U.S. Appl. No. 14/754,632, filed Jun. 29, 2015.
U.S. Appl. No. 12/948,028, filed Nov. 17, 2011.

\* cited by examiner

THEORETICAL VALUE
C18H29N6O4Se2

| INT. | 0.0268 | 0.0060 | 0.5733 | 0.5375 | 4.2090 | 5.4633 | 20.0951 | 16.2818 | 51.9135 | 36.3525 | 24.2165 | 90.3920 | 100.0000 | 21.6982 | 33.4032 | 7.1097 | 3.7986 | 0.7327 | 0.0984 | 0.0102 | 0.0009 |
|---|---|---|---|---|---|---|---|---|---|---|---|---|---|---|---|---|---|---|---|---|---|
| m/z | 541.0700 | 542.0727 | 543.0667 | 544.0678 | 545.0641 | 545.0646 | 547.0625 | 548.0630 | 549.0607 | 550.0620 | 551.0594 | 552.0619 | 553.0584 | 554.0611 | 555.0587 | 555.0612 | 557.0598 | 558.0619 | 559.0640 | 560.0662 | 561.0685 |

FIG. 2 CONT.

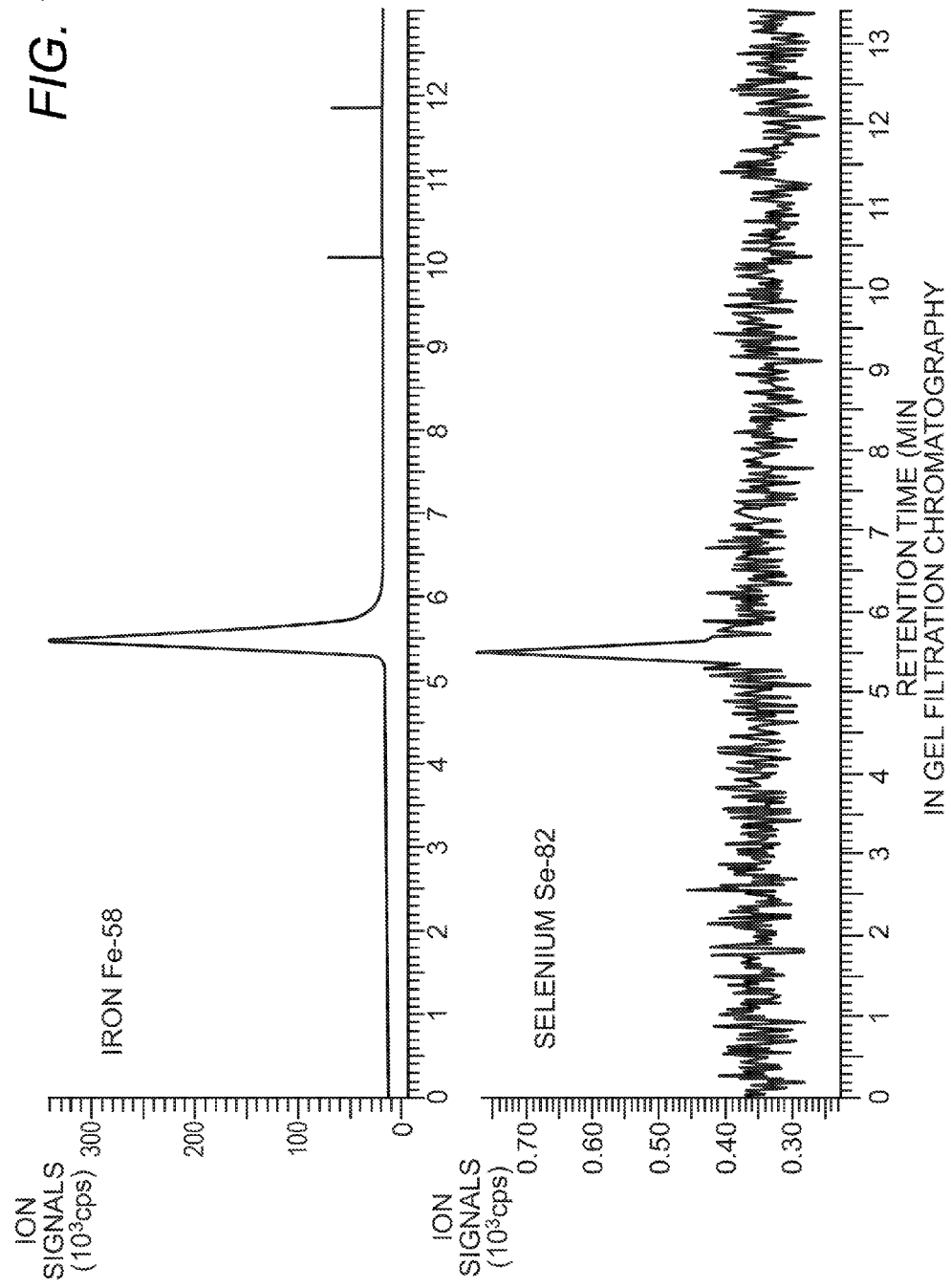

SELENIUM-CONTAINING COMPOUND

CROSS-REFERENCE TO RELATED APPLICATIONS

This patent application is a continuation of copending U.S. patent application Ser. No. 14/754,632, filed on Jun. 29, 2015, which is a continuation of U.S. patent application Ser. No. 12/948,028, filed on Nov. 17, 2010, now U.S. Pat. No. 9,109,158, issued on Aug. 18, 2015, which claims the benefit of Japanese Patent Application No. 2009-282034, filed Dec. 11, 2009, which are incorporated by reference in their entireties herein.

BACKGROUND OF THE INVENTION

The present invention relates to a novel selenium-containing compound. The invention also relates to a method of producing the selenium-containing compound, use of the selenium-containing compound as an antioxidant, and an analysis method that uses the selenium-containing compound as a standard substance.

Selenium is an essential trace element for humans. Selenium forms enzymes and proteins in vivo, and plays an important role in antioxidant reactions (Non-patent Documents 1 and 2). Selenium is abundant in algae, fish, shellfish, meat, and egg yolk (Non-patent Document 3). Selenium is also abundant in the meat of various fish species generally consumed by the Japanese (Non-patent Documents 1 to 4).

It is known that the dark muscle of tuna and whale meat contain selenium in high concentration (Non-patent Documents 5 to 7). The selenium content in each internal organ of *Thunnus orientalis* (Pacific bluefin tuna) has been reported (e.g., blood (15.2 ppm), kidney (8.3 ppm), spleen (7.6 ppm), superficial dark muscle (6.1 ppm), true dark muscle (5.9 ppm), heart superficial dark muscle (4.4 ppm), liver superficial dark muscle (4.1 ppm), gills (2.6 ppm), brain (1.4 ppm), and ordinary muscle (0.57 ppm)). Since the selenium content exceeds 4 ppm in some internal organs, these internal organs may be used as an organic selenium source (Non-patent Document 8). However, since the biochemical properties of selenium in each internal organ are unclear, and it is difficult to obtain a high-purity extract, these internal organs have not been effectively utilized as an organic selenium source.

Since selenium is normally present in food as a selenocysteine residue (i.e., a constituent amino acid of a protein), it is considered that selenium is digested and absorbed when absorption of the protein occurs. Therefore, the absorption of selenium in food from a digestive tract is estimated to be 50% or more (Non-patent Document 1). About 250 µg/kg of selenium is present in the human body, and in vivo selenium homeostasis is maintained through excretion into urine (Non-patent Document 1).

The selenocysteine residue of an enzyme/protein is positioned at a selenol group (i.e., active center) of a selenoprotein. Selenoproteins (e.g., glutathione peroxidase and thioredoxin reductase that decompose and remove active oxygen and hydroperoxides, 5'-iodothyronine deiodinase that is involved in production of thyroid hormones, and selenoprotein P that is present in plasma) play an important role in an in vivo antioxidant effect (Non-patent Document 1). It has been considered based on the above findings that organic selenium included in fish meat at a high concentration is a selenoprotein (e.g., glutathione peroxidase) or a peptide/amino acid thereof (Patent Document 1).

When selenium deficiency has occurred, cellular disorder occurs due to peroxides (Non-patent Document 1). The onset of cardiomyopathy (Keshan disease) (i.e., selenium deficiency disease) observed in the selenium-deficient northeast part of China is prevented by administration of selenious acid (Non-patent Document 1). Kaschin-Beck disease (Beck's disease) that manifests in adolescence and is observed in selenium-deficient northern China and Siberia is also caused by selenium deficiency (Non-patent Document 1).

It has been reported that selenium deficiency has a correlation with coronary artery diseases (i.e., angina pectoris and heart infarction) based on an epidemiological study that compares the incidence of heart diseases with the selenium level in blood. It has been reported that the rate of deaths from cardiovascular diseases due to selenium deficiency is high in eastern Finland, and a group with a serum selenium level of 45 µg/l or less has a high incidence of heart diseases (Non-patent Document 1).

It is known that muscle pains, skin dryness, liver necrosis, and the like are caused by selenium deficiency (Non-patent Document 1). It has been reported that selenium deficiency increases the risk of cancer such as lung cancer, large bowel cancer, prostate cancer, rectal cancer, breast cancer, and leukocythemia (Non-patent Documents 1 and 10). It has been reported that the cellular immune response to cancer cells is enhanced by administering 200 µg/day of sodium selenite during surgical therapy or radiotherapy of cancer (Non-patent Document 8). It has also been reported that selenium acts on the cancer cell signaling system to suppress cell growth, and induces apoptosis (Non-patent Document 1). Non-patent Document 12 points out that 100 to 200 µg/day of selenium suppresses DNA mutation and oxidative damage due to carcinogens to suppress the progress of cancer, but an intake of more than 400 µg/day of selenium may be harmful. It has thus been considered that selenium is effective for suppressing or treating cancer, or preventing recurrence of cancer.

On the other hand, excessive intake of selenium is toxic, and may cause nail deformation, unhairing, gastrointestinal injury, neuropathy, heart infarction, acute respiratory distress, renal insufficiency, and the like (Non-patent Document 1).

As the dietary reference intakes of selenium, the estimated average requirement is set to 25 (20) µg, the recommended dietary allowance is set to 30 (25) µg, and the upper limit is set to 450 (350) µg (the values are for adult men (the value in parentheses is the estimated average requirement for adult women)) (Ministry of Health, Labour and Welfare, Nov. 22, 2004, Non-patent Document 13). Note that the estimated average requirement and the recommended dietary allowance for a 30 to 49-year-old male is 30 µg and 35 µg, respectively (Non-patent Document 13). In Japan, the selenium upper limit is set to 100 to 450 µg Se/day taking account of the value (800 µg Se/day) obtained by the study on Enshi, Hubei Province in China using unhairing and nail brittleness/loss as indices (Non-patent Documents 13 and 16).

In recent years, an organic selenium-containing supplement that includes inorganic selenium and selenomethionine as active ingredients has been used to treat or prevent diseases due to selenium deficiency. Selenium-containing yeast that is obtained by culturing yeast in a culture medium including inorganic selenium, and includes selenomethionine at a high concentration has been used as an organic selenium-containing compound supply source (Non-patent Document 1). Such selenium-containing yeast has been used to increase the selenium content in food, a cosmetic preparation, and feed.

Organic selenium can be extracted from a raw material (e.g., meat or internal organs of fish) having a selenium content of more than 0.5 ppm in order to supply selenium that can be efficiently used for humans, livestock, fish, and shellfish. A selenium-containing material having a selenium content of more than 5 ppm can be provided by freeze-drying these tissues or concentrating an extract thereof. A protein concentrate and a hydrochloric acid hydrolyzate having a total selenium content of about 18 to 103.5 ppm has been obtained from dark muscle (Patent Document 1). However, since the muscles and the internal organs of large fish and carnivorous fish such as tuna contain methylmercury at a relatively high concentration of more than 0.5 ppm, an unpurified dry powder, freeze-dried product, concentrate, protease hydrolyzate, and the like thereof contain selenium at a relatively high concentration, but also contain methylmercury at a high concentration. Moreover, the internal organs of fish and shellfish have a cadmium content of 1 ppm or more. Specifically, since the dark muscles and the internal organs of fish and shellfish may contain methylmercury and cadmium (toxic heavy metals), the dark muscles and the internal organs of fish and shellfish cannot be suitably used for drugs, food, feed, and the like. Therefore, it is necessary to remove toxic heavy metals by purification from an organic selenium-containing compound derived from a fish/shellfish tissue concentrate/extract.

Non-patent Document 14 discloses a method that analyzes selenium in a living body and food by performing thermal wet-digestion using a mixture of nitric acid and perchloric acid, reacting the resulting product with 2,3-diaminonaphthalene (DAN), and utilizing the fluorescence of 4,5-benzopiaselenol (Se-DAN) produced by a complex-forming reaction with Se(IV). Non-patent Document 15 discloses a method that identifies the molecular species of inorganic and organic selenium in the environment using an ICP-MS that is connected to an HPLC online. However, a method that analyzes organic selenium-containing compounds including proteins and amino acids in a living body and food at the same time has not been proposed.

Selenium has been industrially used as a photoreceptor/semiconductor material, a red to orange pigment for glass, ceramics, and plastics, a decolorizer and an anti-foaming agent used for glass production, a metallurgical additive, and the like (Non-patent Document 16).

RELATED-ART DOCUMENT

Patent Document

Patent Document 1: JP-A-2001-231498

Non-Patent Document

Non-patent Document 1: Seiichiro Himeno: Selenium, "Nutrition of minerals/trace elements", edited by Tsugumi Suzuki and Osamu Wada, DAI-ICHI SHUPPAN Co., Ltd., pp. 423-445, 1994
Non-patent Document 2: Gerald F., Jr. Combs: Selenium in global food systems, British Journal of Nutrition, 85(5), pp. 517-547 (2001)
Non-patent Document 3: Gerald F., Jr. Combs: The Role of Selenium in Nutrition, Academic Press, pp. 1-532, 1986
Non-patent Document 4: Yasuo Suzuki (editor), Table of trace element contents in Japanese foodstuffs, DAI-ICHI SHUPPAN Co., Ltd., pp. 1-169, 1993
Non-patent Document 5: Satoshi Arima and Katsuo Nagakura, Mercury and selenium content in toothed whales, Nippon Suisan Gakkaishi, 45, pp. 623-626, 1979
Non-patent Document 6: Yumiko Yamashita, Food chemical research on essential trace elements in fish, Marine product processing research result/program summary (1993), National Research Institute of Fisheries Science, Fisheries Agency, pp. 10-11, February 1994
Non-patent Document 7: Yumiko Yamashita, Food chemical research on essential trace elements in fish, Marine product processing research result/program summary (1996), National Research Institute of Fisheries Science, Fisheries Agency, pp. 28-29, February 1997
Non-patent Document 8: L. Kiremidjian-Schumacher and M. Roy, Effect of selenium on the immunocompetence of patients with head and neck cancer and on adoptive immunotherapy of early and established lesions, Biofactors, 14 (1-4), pp. 161-168 (2001)
Non-patent Document 9: J. T. Salonen, G. Alfthan, J. K. Huttunen, J. Pikkarainen, and P. Puska, Association between cardiovascular death and myocardial infarction and serum selenium in a watched-pair longitudinal study, Lancet, 2, pp. 175-179 (1982)
Non-patent Document 10: Yoshikazu Kawakami, Vitamin E and respiratory diseases, CLINICIAN, 356, pp. 63-66 (1986)
Non-patent Document 11: A. Ghose, J. Fleming, and P R. Harrison, Selenium and signal transduction: roads to cell death and anti-tumour activity, Biofactors, 14 (1-4), pp. 127-133 (2001)
Non-patent Document 12: K. El-Bayoumy, The protective role of selenium on genetic damage and on cancer., Mutat. Res. 475 (1-2), pp. 123-139 (2001)
Non-patent Document 13: Ministry of Health, Labour and Welfare, Dietary Reference Intakes for Japanese, Nov. 22, 2004
Non-patent Document 14: J. H. Watkinson, Fluorometric determination of selenium in biological material with 2,3-diaminonaphthalene. Anal. Chem., 38(1), pp. 92-97 (1966)
Non-patent Document 15: H. Ge, X. J. Cai, J. F. Tyson, P. C. Uden, E. R. Denoyer, and E. Block, Anal. Commun. 33 (1996) 279
Non-patent Document 16: Selenium and its compounds, Chemical Management Center, National Institute of Technology and Evaluation, http://www.safe.nite.go.jp/management/search/Fundamental/76

SUMMARY OF THE INVENTION

An object of the invention is to provide a selenium-containing compound. Another object of the invention is to provide a method of producing the selenium-containing compound, use of the selenium-containing compound as an antioxidant, and an analysis method that uses the selenium-containing compound as a standard substance.

The inventors of the invention conducted extensive studies in order to achieve the above objects, and found a novel selenium-containing compound having a strong in vivo antioxidant effect. The novel selenium-containing compound was obtained by extracting a selenium concentrate from a biological sample (e.g., fish) using an organic solvent, and isolating/purifying a selenium-containing compound in the selenium concentrate by chromatography.

The inventors also found that the selenium-containing compound can be isolated and quantitatively determined by column chromatography, mass spectrometry, or the like, and made it possible to provide an analysis method that uses the selenium-containing compound as a standard substance. A protein to which selenium is specifically bound, or a selenium-containing compound distributed in a living body and food, can be analyzed by this analysis method.

Specifically, the invention relates to the following selenium-containing compound and the like recited in (1) to (58).
(1) A selenium-containing compound shown by the following chemical formula 1,

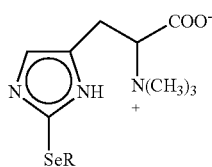

Chemical formula 1 wherein R is absent, or represents hydrogen or an organic compound.
(2) The selenium-containing compound according to (1), the selenium-containing compound being shown by the following chemical formula 2, 3, or 4.

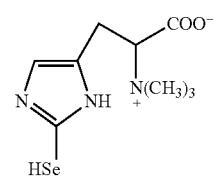

Chemical formula 2

3-(2-hydroseleno-1H-imidazol-5-yl)-
2-(trimethylammonio)propanoate

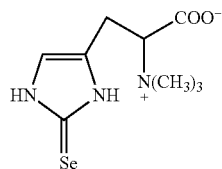

Chemical formula 3

3-(2-selenoxo-2,3-dihydro-1H-imidazol-4-yl)-
2-(trimethylammonio)propanoate

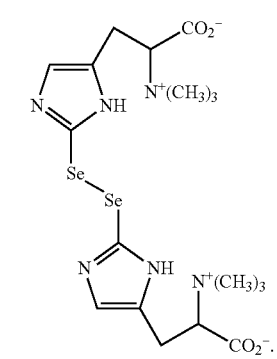

Chemical formula 4

3,3'-(2,2'-diselanediylbis(1H-imidazole-5,2-diyl))bis(2-
(trimethylammonio)propanoate)

(3) A method of analyzing a selenium-containing compound including analyzing a selenium-containing compound using the selenium-containing compound according to (1) or (2) as a standard substance.

(4) A drug, a functional food, a nutritional supplement, a food additive, an animal drug, a feed additive, or a cosmetic preparation including the selenium-containing compound according to (1) or (2).
(5) A medium additive including the selenium-containing compound according to (1) or (2).
(6) An antioxidant including the selenium-containing compound according to (1) or (2).
(7) A methemoprotein formation inhibitor including the selenium-containing compound according to (1) or (2).
(8) An artificial blood that includes hemoglobin or an oxygen carrier having an effect equivalent to that of hemoglobin, a transfusion preparation, or a tissue preservation solution produced using the selenium-containing compound according to (1) or (2).
(9) A fluorescent substance, a UV absorber, or a chemical modifier including the selenium-containing compound according to (1) or (2).
(10) A selenium concentrate including the selenium-containing compound according to (1) or (2).
(11) A method of producing the selenium-containing compound according to (1) or (2), the method including extracting the selenium-containing compound according to (1) or (2) from a sample using an organic solvent or water.
(12) The method according to (11), including extracting the selenium-containing compound according to (1) or (2) from the sample using a hydrophilic organic solvent, followed by extraction with a solvent including a hydrophobic organic solvent.
(13) The method according to (11), wherein the hydrophilic organic solvent is at least one compound selected from ethanol, methanol, acetone, and acetonitrile, and the hydrophobic organic solvent is at least one compound selected from diethyl ether, tetrahydrofuran, cyclohexane, and dichloromethane.
(14) The method according to (12), wherein the hydrophilic organic solvent is at least one compound selected from ethanol, methanol, acetone, and acetonitrile, and the hydrophobic organic solvent is at least one compound selected from diethyl ether, tetrahydrofuran, cyclohexane, and dichloromethane.
(15) The method according to (11), further including reducing the sample that includes the selenium-containing compound according to (1) or (2), or a selenium concentrate that includes the selenium-containing compound according to (1) or (2), using a reducing agent.
(16) The method according to (12), further including reducing a sample that includes the selenium-containing compound according to (1) or (2), or a selenium concentrate that includes the selenium-containing compound according to (1) or (2), using a reducing agent.
(17) The method according to (13), further including reducing a sample that includes the selenium-containing compound according to (1) or (2), or a selenium concentrate that includes the selenium-containing compound according to (1) or (2), using a reducing agent.
(18) The method according to (14), further including reducing a sample that includes the selenium-containing compound according to (1) or (2), or a selenium concentrate that includes the selenium-containing compound according to (1) or (2), using a reducing agent.
(19) The method according to (16), wherein the reducing agent is a thiol reducing agent.
(20) The method according to (17), wherein the reducing agent is a thiol reducing agent.
(21) The method according to (18), wherein the reducing agent is a thiol reducing agent.

(22) The method according to (19), wherein the reducing agent is a thiol reducing agent.
(23) The method according to (11), further including concentrating a selenium concentrate using an ion-exchange resin.
(24) The method according to (12), further including concentrating a selenium concentrate using an ion-exchange resin.
(25) The method according to (13), further including concentrating a selenium concentrate using an ion-exchange resin.
(26) The method according to (14), further including concentrating a selenium concentrate using an ion-exchange resin.
(27) The method according to (15), further including concentrating a selenium concentrate using an ion-exchange resin.
(28) The method according to (16), further including concentrating a selenium concentrate using an ion-exchange resin.
(29) The method according to (17), further including concentrating a selenium concentrate using an ion-exchange resin.
(30) The method according to (18), further including concentrating a selenium concentrate using an ion-exchange resin.
(31) The method according to (19), further including concentrating a selenium concentrate using an ion-exchange resin.
(32) The method according to (20), further including concentrating a selenium concentrate using an ion-exchange resin.
(33) The method according to (21), further including concentrating a selenium concentrate using an ion-exchange resin.
(34) The method according to (22), further including concentrating a selenium concentrate using an ion-exchange resin.
(35) The method according to (11), further including purifying a selenium concentrate by high performance liquid chromatography (HPLC).
(36) The method according to (12), further including purifying a selenium concentrate by high performance liquid chromatography (HPLC).
(37) The method according to (13), further including purifying a selenium concentrate by high performance liquid chromatography (HPLC).
(38) The method according to (14), further including purifying a selenium concentrate by high performance liquid chromatography (HPLC).
(39) The method according to (15), further including purifying a selenium concentrate by high performance liquid chromatography (HPLC).
(40) The method according to (16), further including purifying a selenium concentrate by high performance liquid chromatography (HPLC).
(41) The method according to (17), further including purifying a selenium concentrate by high performance liquid chromatography (HPLC).
(42) The method according to (18), further including purifying a selenium concentrate by high performance liquid chromatography (HPLC).
(43) The method according to (19), further including purifying a selenium concentrate by high performance liquid chromatography (HPLC).
(44) The method according to (20), further including purifying a selenium concentrate by high performance liquid chromatography (HPLC).
(45) The method according to (21), further including purifying a selenium concentrate by high performance liquid chromatography (HPLC).
(46) The method according to (22), further including purifying a selenium concentrate by high performance liquid chromatography (HPLC).
(47) The method according to (23), further including purifying a selenium concentrate by high performance liquid chromatography (HPLC).
(48) The method according to (24), further including purifying a selenium concentrate by high performance liquid chromatography (HPLC).
(49) The method according to (25), further including purifying a selenium concentrate by high performance liquid chromatography (HPLC).
(50) The method according to (26), further including purifying a selenium concentrate by high performance liquid chromatography (HPLC).
(51) The method according to (27), further including purifying a selenium concentrate by high performance liquid chromatography (HPLC).
(52) The method according to (28), further including purifying a selenium concentrate by high performance liquid chromatography (HPLC).
(53) The method according to (29), further including purifying a selenium concentrate by high performance liquid chromatography (HPLC).
(54) The method according to (30), further including purifying a selenium concentrate by high performance liquid chromatography (HPLC).
(55) The method according to (31), further including purifying a selenium concentrate by high performance liquid chromatography (HPLC).
(56) The method according to (32), further including purifying a selenium concentrate by high performance liquid chromatography (HPLC).
(57) The method according to (33), further including purifying a selenium concentrate by high performance liquid chromatography (HPLC).
(58) The method according to (34), further including purifying a selenium concentrate by high performance liquid chromatography (HPLC).

The novel selenium-containing compound obtained by the invention may be used as a standard substance for analyzing biological components and food. The selenium content in a living body and food can be measured for each chemical form by analyzing a selenium-containing protein, a selenium-containing peptide, a selenium-containing amino acid, and inorganic selenious acid in a living body and food using the selenium-containing compound. Since the selenium-containing compound according to the invention is safe and has high bioavailability as compared with selenious acid and the like, selenium can be efficiently incorporated in a living body such as humans, livestock, fish, and shellfish. Since the selenium-containing compound according to the invention exhibits an in vivo antioxidant effect equal to or higher than that of known antioxidants, the selenium-containing compound may be used as an active ingredient of a drug, a functional food, a nutritional supplement, a food additive, an animal drug, a feed additive, a cosmetic preparation, and the like, as an antioxidant that improves an in vivo antioxidant effect in a redox pathway that involves selenium.

BRIEF DESCRIPTION OF THE DRAWINGS

FIG. 1 shows a process that isolates a selenium concentrate derived from the dark muscle of *Thunnus obesus*.

FIG. 12 is a view showing iron and selenium detected from myoglobin (Example 5).

DESCRIPTION OF EXEMPLARY EMBODIMENTS

Figure 1:
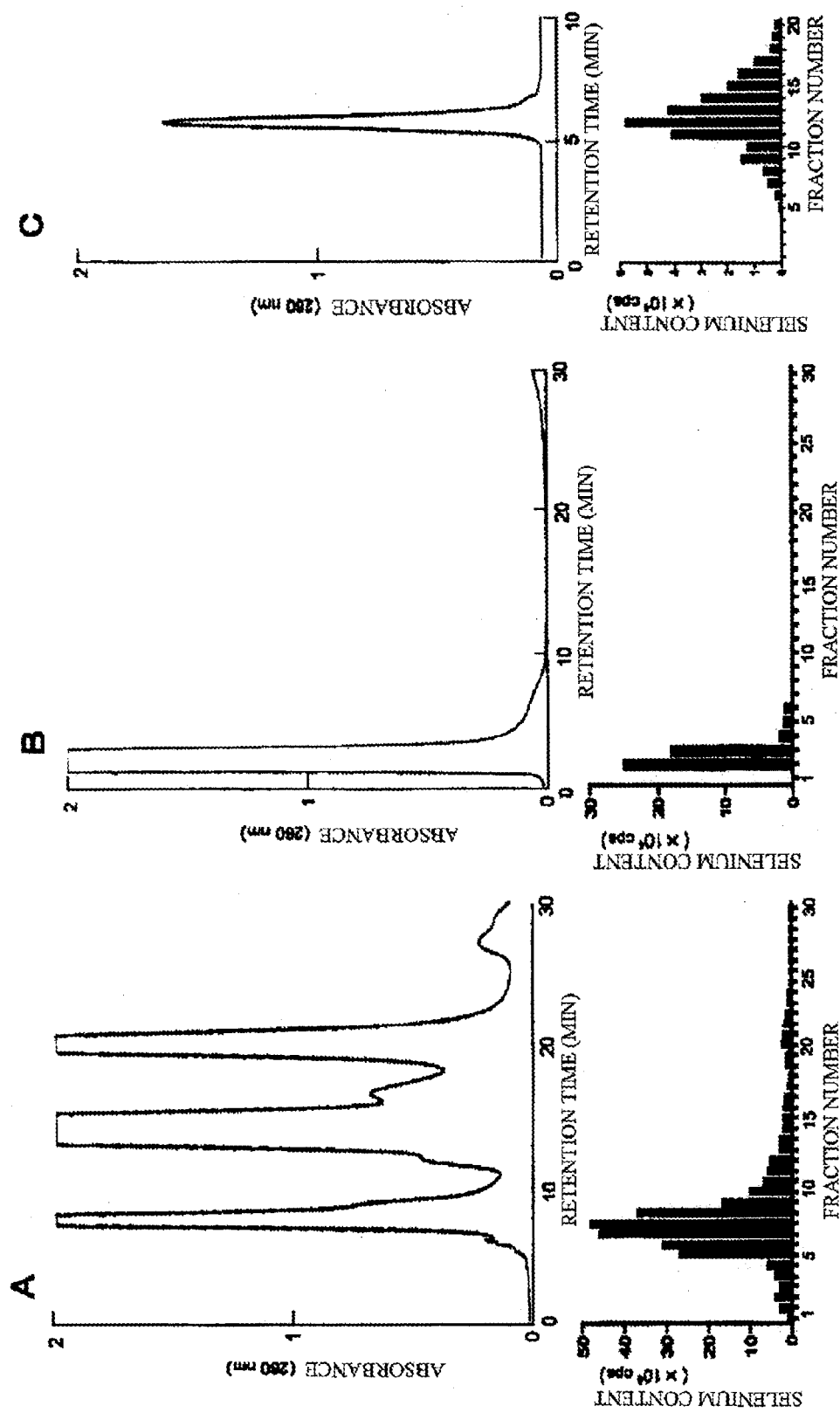
FIG. 1 is a view showing a process of purifying a selenium-containing compound by HPLC from a selenium concentrate derived from the dark muscle of *Thunnus obesus* (Example 1).

A selenium-containing compound according to one embodiment of the invention includes a skeleton shown by the chemical formula 1, wherein R represents hydrogen or an organic compound. For example, the selenium-containing compound may be a selenium-containing compound shown by the chemical formula 2 (3-(2-hydroseleno-1H-imidazol-5-yl)-2-(trimethylammonio)propanoate) or a selenium-containing compound shown by the chemical formula 3 (3-(2-selenoxo-2,3-dihydro-1H-imidazol-4-yl)-2-(trimethylammonio)propanoate). The selenium-containing compound shown by the chemical formula 2 or 3 is a monomer of the selenium-containing compound. The selenium-containing compound shown by the chemical formula 2 has a molecular structure in which a selenol group is bonded to a carbon atom at position 2 of a pyrimidine ring. Since a selenol group forms a tautomer that is in an equilibrium state with a selenoketone group, the selenium-containing compound may have a selenol-type chemical form (chemical formula 2) and a selenoketone-type chemical form (chemical formula 3) in a solution state depending on the solvent conditions. An oxidized dimer is easily formed in a non-polar solvent in which the equilibrium shifts to the selenol isomer, and the chemical equilibrium shifts to the selenoketone isomer in a polar solvent so that the selenium-containing compound is mainly present as a monomer.

The selenium-containing compound according to one embodiment of the invention also includes a dimer shown by the chemical formula 4 (oxidized dimer: 3,3'-(2,2'-diselanediylbis(1H-imidazole-5,2-diyl))bis(2-(trimethylammonio)propanoate)) in which compounds (basic units) having a molecular structure in which a selenol group and a trimethylammonium group are bonded to a pyrimidine ring form a diselenide through the selenol groups.

The selenium-containing compound according to one embodiment of the invention also includes selenium-containing compounds in which ergothioneine, glutathione, cysteine, acetylcysteine, homocysteine, methylmercury, or a thiol compound considered to be produced in vivo is bonded to R, and metal or polymer materials to which the selenium-containing compound is bonded through the selenol group, in addition to the selenium-containing compounds shown by the chemical formulas 2 to 4.

A method of analyzing a selenium-containing compound according to one embodiment of the invention includes analyzing a selenium-containing protein (e.g., glutathione peroxidase or selenoprotein P), a selenium-containing peptide, a selenium-containing amino acid (e.g., selenocystine or selenomethionine), an organic or inorganic selenious acid (e.g., the selenium-containing compound according to one embodiment of the invention (selenoneine)), or the like included in a living body, food, or drink (i.e., measurement target) using the selenium-containing compound according to one embodiment of the invention as a standard substance.

For example, the selenium-containing compound according to one embodiment of the invention is isolated and purified by chromatography, and introduced into an ICP-MS online to ionize selenium. A selenoprotein, a selenium-containing amino acid, selenious acid, and organic and inorganic selenium included in the measurement target can thus be analyzed and measured at the same time (see FIGS. 5 and 6).

A selenium-containing compound included in a living body or food may be isolated by chromatography under arbitrary conditions insofar as a selenoprotein, a selenium-containing amino acid, selenious acid, and organic and inorganic selenium can be analyzed and measured. For example, the selenium content in each chemical form may be quantitatively analyzed by isolating a living tissue extract using a gel-filtration column ("Ultrahydrogel 120" manufactured by Waters Co., inner diameter: 7.8 mm, column length: 300 mm) that is equilibrated with 0.1 M ammonium formate (see FIG. 7).

The selenium-containing compound according to one embodiment of the invention may be included in a drug, a functional food, a nutritional supplement, a food additive, an animal drug, a feed additive, a cosmetic preparation, a medium additive, an antioxidant, and the like as an active ingredient. The selenium-containing compound according to one embodiment of the invention may be included in a methemoprotein formation inhibitor, an artificial blood including hemoglobin or an oxygen carrier having an effect equivalent to that of hemoglobin, a transfusion preparation, a tissue preservation solution, a fluorescent substance, a UV absorber, a chemical modifier, and the like as an active ingredient. A selenium concentrate including a selenium-containing compound obtained when producing the selenium-containing compound according to one embodiment of the invention may also be used as a raw material including an active ingredient.

The drug that includes the selenium-containing compound according to one embodiment of the invention may be a preventive preparation, a therapeutic agent, and the like that is effective for diseases considered to be caused by selenium deficiency as an antioxidant that improves an in vivo antioxidant effect in a redox pathway that involves selenium. Examples of diseases that are considered to be caused by selenium deficiency include cancers such as lung cancer, prostate cancer, and large bowel cancer, heart diseases, diabetes, and the like.

For example, it is known that the onset of (or death from) cardiomyopathy (Keshan disease) observed in a selenium-deficient area in China at an altitude of 1000 meters or more is improved by intake of selenious acid. Cardiomyopathy (Keshan disease) is considered to occur when the selenium-containing compound according to one embodiment of the invention bound to myoglobin and hemoglobin becomes deficient under low-oxygen conditions so that auto-oxidation of heme iron and radical formation occur to a large extent. It has been reported that the rate of deaths from cardiovascular diseases due to selenium deficiency is high in eastern Finland, and a group with a serum selenium level of 45 µg/l or less has a high incidence of heart diseases (Non-patent Document 1).

It is conjectured that the risk of heart diseases can be reduced by improving an in vivo antioxidant effect in a redox pathway that involves selenium via administration of the drug that includes the selenium-containing compound according to one embodiment of the invention.

It is known that the selenium intake level and the cancer mortality rate have a negative correlation. Studies conducted in Finland and the United States suggest that the cancer mortality rate of a group with a low serum selenium level increases by a factor of 2 to 3 (Non-patent Document 1). It is conjectured that the risk of cancer due to selenium deficiency can be reduced by improving an in vivo antioxidant effect in a redox pathway that involves selenium by providing the drug that includes the selenium-containing compound.

The animal drug that includes the selenium-containing compound according to one embodiment of the invention may be a preventive preparation, a therapeutic agent, and the like effective for animal diseases that are considered to be caused by selenium deficiency by improving an in vivo antioxidant effect in a redox pathway that involves selenium. These preventive preparations, therapeutic agents, and the like can be provided in the same manner as the drug that includes the selenium-containing compound according to one embodiment of the invention.

The functional food that includes the selenium-containing compound according to one embodiment of the invention includes any type of food that includes the selenium-containing compound according to one embodiment of the invention, and is useful for preventing or reducing (treating) symptoms of diseases that are considered to be caused by selenium deficiency by improving an in vivo antioxidant effect in a redox pathway that involves selenium, and it is permitted to specify to that effect.

The nutritional supplement that includes the selenium-containing compound according to one embodiment of the invention includes any type of nutritional supplement that includes the selenium-containing compound according to one embodiment of the invention, and prevents selenium deficiency. Examples of the nutritional supplement include nutritional supplements and the like to which the selenium-containing compound according to one embodiment of the invention is added in an amount of about 50 to about 200 µg (i.e., an amount necessary for preventing selenium deficiency).

The food additive that includes the selenium-containing compound according to one embodiment of the invention, or the feed additive that includes the selenium-containing compound according to one embodiment of the invention, includes any type of food additive or feed additive that includes the selenium-containing compound according to one embodiment of the invention, and is added to food or feed in order to prevent selenium deficiency by improving an in vivo antioxidant effect in a redox pathway that involves selenium.

The cosmetic preparation that includes the selenium-containing compound according to one embodiment of the invention includes any type of cosmetic preparation that includes the selenium-containing compound according to one embodiment of the invention, and is used to solve beauty problems by improving an in vivo antioxidant effect in a redox pathway that involves selenium.

The selenium-containing compound according to one embodiment of the invention is a selenium source that has very low cytotoxicity as compared with sodium selenite and selenomethionine that have been used for the above applications, does not include a toxic heavy metal, and is easily absorbed into a living body. Therefore, the selenium-containing compound according to one embodiment of the invention is very useful.

It was confirmed by a chemical test that the selenium-containing compound according to one embodiment of the invention is a substance that has a very strong antioxidant ability, and has a radical-scavenging ability higher than that of a water-soluble vitamin E derivative "Trolox" (registered trademark) (6-hydroxy-2,5,7,8-tetrametylchroman-2-carboxylic acid) by a factor of about 500. It is conjectured that the selenium-containing compound according to one embodiment of the invention has a DNA repair effect. Therefore, the selenium-containing compound according to one embodiment of the invention may be used as an antioxidant, and may also be used to provide a functional food, a nutritional supplement, a food additive, or a cosmetic preparation that achieves an anti-aging effect by improving an in vivo antioxidant effect in a redox pathway that involves selenium.

Selenious acid, selenocystine, selenomethionine, and the like have also been used for administration tests on living organisms. The selenium-containing compound according to one embodiment of the invention is a safe and useful substance that has high bioavailability and very low cytotoxicity as compared with selenious acid, selenocystine, selenomethionine, and the like.

The medium additive that includes the selenium-containing compound according to one embodiment of the invention includes any type of medium additive that can be added as a selenium source or an antioxidant to a culture medium used when artificially culturing animal cells, plant cells, and microorganisms.

The selenium-containing compound according to one embodiment of the invention is specifically introduced into cells (e.g., vessel endothelial cells or red cells), and has low cytotoxicity. Therefore, the selenium-containing compound according to one embodiment of the invention may be used as a medium additive that is added to a serum-free medium or a low-serum medium for animal cells instead of selenious acid.

The selenium-containing compound according to one embodiment of the invention is an organic cationic betaine compound having a chemical structure similar to that of ergothioneine, carnitine, and the like, is promptly introduced into cells from a culture medium in a cell culture test, and promotes cell growth. It is conjectured that transport inside and outside the cells is controlled by an organic cation/carnitine transporter (OCTN) (I. Tamai et al., Mol. Pharm. 1, pp. 57-66 (2003), and D. Grundemann et al., Discovery of the ergothioneine transporter, PNAS, 102, pp. 5256-5261 (2005)).

The methemoprotein formation inhibitor that includes the selenium-containing compound according to one embodiment of the invention includes any type of substance that includes the selenium-containing compound according to one embodiment of the invention, and inhibits methemoprotein formation.

The transfusion preparation, the tissue preservation solution, or the artificial blood using the selenium-containing compound according to one embodiment of the invention includes any type of transfusion preparation or tissue preservation solution that includes the selenium-containing compound according to one embodiment of the invention, or any type of artificial blood that includes hemoglobin or an oxygen carrier having an effect equivalent to that of hemoglobin. Examples of the oxygen carrier having an effect equivalent to that of hemoglobin include a hemoglobin-containing ribosome, a porphyrin metal complex-albumin complex, a polyethylene glycolated (PEG) porphyrin metal complex-albumin complex, crosslinked hemoglobin, a hemoglobin polymer, a polyethylene glycolated hemoglobin polymer, and the like.

Since the selenium-containing compound according to one embodiment of the invention functions as an antioxidant or a heme iron auto-oxidation inhibitor, the selenium-containing compound according to one embodiment of the invention may be used when storing blood, organs, or artificial blood.

Nutrition therapy (e.g., total parenteral nutrition) has been used when treating digestive system diseases. It has been reported that nutrition therapy results in deficiency of trace elements (Non-patent Document 1). In this case, when adding the selenium-containing compound according to one embodiment of the invention to a component of the transfusion preparation, the selenium-containing compound is circulated through the body via blood, and introduced into tissues and cells, so that selenium deficiency can be prevented.

The fluorescent substance, the UV absorber, or the chemical modifier that includes the selenium-containing compound according to one embodiment of the invention includes any type of substance that includes the selenium-containing compound according to one embodiment of the invention, and can be used as a fluorescent substance, a UV absorber, or a chemical modifier. Since the selenium-containing compound according to one embodiment of the invention includes a selenol group having higher reactivity than that of a thiol group, and has fluorescent and UV absorption characteristics, and the like, the selenium-containing compound according to one embodiment of the invention may be used as various industrial materials (e.g., fluorescent substance, UV absorber, or chemical modifier).

The method of producing the selenium-containing compound according to one embodiment of the invention includes extracting the selenium-containing compound shown by any of the chemical formulas 1 to 4, or a selenium concentrate including the selenium-containing compound shown by any of the chemical formulas 1 to 4 from a sample using water or an organic solvent.

The selenium concentrate including the selenium-containing compound according to one embodiment of the invention refers to a selenium concentrate including the selenium-containing compound shown by any of the chemical formulas 1 to 4 obtained when producing the selenium-containing compound according to one embodiment of the invention. For example, the selenium concentrate including the selenium-containing compound according to one embodiment of the invention may be obtained by obtaining an extract from a sample using an organic solvent or water, and concentrating the extract using a rotary evaporator or the like. When the selenium concentrate including the selenium-containing compound according to one embodiment of the invention is a solution, it is preferable that the selenium concentrate includes the selenium-containing compound according to one embodiment of the invention in an amount of 5 µg/ml or more. The selenium concentrate may also include ergothioneine that has chemical properties similar to those of the selenium-containing compound according to one embodiment of the invention.

In the method of producing the selenium-containing compound according to one embodiment of the invention, the selenium-containing compound may be extracted from the sample using water or an organic solvent by immersing the sample in an organic solvent (e.g., acetone, ethanol, or methanol), water, or the like, optionally crushing the tissues in the solvent, and collecting a soluble fraction including the selenium-containing compound shown by any of the chemical formulas 1 to 4 dissolved in the solvent by centrifugation, filtration, or the like.

The above step may further include concentrating the collected soluble fraction by vacuum concentration, membrane separation, electrodialysis, chromatography, or freeze-drying.

The type of organic solvent used for extraction, the number of extraction operations, and the like are not particularly limited insofar as the selenium-containing compound shown by any of the chemical formulas 1 to 4 or a selenium concentrate including the selenium-containing compound shown by any of the chemical formulas 1 to 4 can be obtained from the sample. It is preferable that the method include extracting the selenium-containing compound from the sample using a hydrophilic organic solvent, followed by extraction with a solvent including a hydrophobic organic solvent. For example, the purity of the selenium-containing compound to be extracted increases by extracting the selenium-containing compound from the sample using ethanol, methanol, or acetone (i.e., hydrophilic organic solvent), followed by extraction with a mixture of acetonitrile (i.e., hydrophilic organic solvent) and diethyl ether (i.e., hydrophobic organic solvent) (i.e., a solvent including a hydrophobic organic solvent).

As the hydrophilic organic solvent, a known hydrophilic organic solvent may be used. For example, the hydrophilic organic solvent may be at least one compound selected from ethanol, methanol, acetone, and acetonitrile. As the hydrophobic organic solvent, a known hydrophobic organic solvent may be used. For example, the hydrophobic organic solvent may be at least one compound selected from diethyl ether, tetrahydrofuran or dichloromethane. The solvent including a hydrophobic organic solvent may be an arbitrary solvent including such a hydrophobic organic solvent, and includes a mixed solvent of a hydrophilic organic solvent and a hydrophobic organic solvent, and a solvent that includes only a hydrophobic organic solvent.

The method of producing the selenium-containing compound according to one embodiment of the invention preferably further includes reducing the sample or the selenium concentrate using a reducing agent since the selenium-containing compound may be strongly bonded (coordinated) to heme iron to form a heme iron complex. The heme iron of the heme iron complex may be removed by extraction with an organic solvent such as acetonitrile, but can be reliably removed using a reducing agent.

The sample or a selenium concentrate including the selenium-containing compound obtained from the sample may be reduced using a reducing agent. It is preferable to reduce the sample or the selenium concentrate using a thiol reducing agent. Examples of the thiol reducing agent include dithiothreitol, 2-mercaptoethanol, glutathione, and the like.

The selenium-containing compound can be isolated by the reduction step using the reducing agent, so that the extraction efficiency from the sample can be increased, and methylmercury (toxic component) can be removed.

The method of producing the selenium-containing compound according to one embodiment of the invention preferably includes concentrating the selenium concentrate using an ion-exchange resin, or concentrating the selenium concentrate by high performance liquid chromatography (HPLC).

The concentration of the selenium-containing compound in the selenium concentrate can be increased by concentrating the selenium concentrate using an ion-exchange resin. The selenium-containing compound shown by any of the chemical formulas 1 to 4 can be obtained by concentrating the selenium concentrate by HPLC.

The selenium-containing compound according to one embodiment of the invention can be purified to high purity by isolating (separating) the selenium concentrate including the selenium containing compound obtained by extraction using water or an organic solvent by chromatography (e.g., silica gel column chromatography, ion-exchange column chromatography, C18 reversed-phase column chromatography, or thin-layer chromatography). The selenium-containing compound according to one embodiment of the invention thus purified to high purity includes selenium in an amount of 20 to 29% (200,000 to 290,000 ppm).

The sample from which the selenium-containing compound according to one embodiment of the invention is extracted is not particularly limited insofar as the sample includes the selenium-containing compound shown by any of the chemical formulas 1 to 4. For example, the selenium-containing compound was detected from squid tissues, fish tissues, bird tissues, and mammal tissues. Therefore, these tissues may be used as the sample optionally in the form of a dried product or a powder.

A large amount of selenium-containing compound is included in the edible part and fishery processing residues (e.g., dark muscle, spleen, hepatopancreas, heart, and blood) of fish and shellfish (e.g., tuna), the internal organs of salmon, *Beryx splendens*, *Todarodes pacificus*, and the like, the internal organs of whales, livestock, and domestic fowl, and the like. Therefore, it is also preferable to use the tissues of these internal organs and the like as the sample optionally in the form of a dried product or a powder.

Specifically, the dark muscle of tuna such as *Thunnus orientalis*, *Thunnus maccoyii*, *Thunnus obesus*, and *Thunnus alalunga*, whale meat such as the lean meat of *Globicephala macrorhynchus*, tuna blood, the hepatopancreas of tuna such as *Thunnus orientalis*, and the like may be used.

A product that is chemically or enzymatically synthesized from amino acids (e.g., histidine, hercynine, and ergothioneine) or betaines that are considered to be located in the same metabolic pathway as the selenium-containing compound according to one embodiment of the invention may also be used as the sample.

The sample may also be microorganisms, cultured cells, animals, or plants that biosynthesize or store the selenium-containing compound according to one embodiment of the invention.

The invention is further described below by way of examples. Note that the invention is not limited to the following examples.

EXAMPLES

Example 1

Extraction of Selenium-Containing Compound

1. Sample

1) Dark muscle: The dark muscle of *Thunnus orientalis*, *Thunnus maccoyii*, *Thunnus obesu*, or *Thunnus alalunga* was used as tuna dark muscle. The dark muscle of *Xiphias gladius* was used as marlin dark muscle.
2) Whale meat: The lean meat of *Globicephala macrorhynchus* was used.
3) Tuna blood: The blood of *Thunnus orientalis* was used.
4) Tuna hepatopancreas: The hepatopancreas of *Thunnus orientalis* was used.

2. Measurement of Selenium Content

The selenium content in the selenium-containing compound or the selenium concentrate including the selenium-containing compound was measured by the following fluorometry.

<Fluorometry>

10 to 100 µl of a sample solution was wet-ashed in a graduated stopper test tube at 210° C. for 2 hours together with 1 ml of a mixed acid (nitric acid:perchloric acid: sulfuric acid=1:2) (hereinafter referred to as "mixed acid"). After the addition of 0.2 ml of a saturated ammonium oxalate aqueous solution, the mixture was heated in a water bath at 100° C. for 5 minutes.

After the addition of 0.2 ml of 6N hydrochloric acid, the mixture was heated in a water bath at 100° C. for 30 minutes. After cooling the mixture with water, 0.2 ml of 0.1 M disodium ethylenediaminetetraacetate was added. The pH of the mixture was adjusted to 1.0 to 1.5 using a 6N sodium hydroxide aqueous solution. After the addition of 1 ml of DAN (1 mg/ml) dissolved in 0.1N hydrochloric acid, the mixture was heated at 50° C. for 20 minutes.

After cooling the mixture with water, the mixture was shaken together with 1 ml of cyclohexane. The fluorescence of the cyclohexane layer was then measured (excitation light: 379 nm, fluorescence wavelength: 521 nm). A calibration curve was drawn by fluorometry using a blank and 5, 10, 50, and 100 µl of a 1 mg/l selenium standard solution, and the selenium content in the sample was calculated.

3. Extraction Method

1) Extraction of Selenium-Containing Compound from Tuna Dark Muscle or Marlin Dark Muscle Step 1: Extraction of Heme Iron Complex of Selenium-Containing Compound The dark muscle of *Thunnus orientalis*, the dark muscle of *Thunnus maccoyii*, the dark muscle of *Thunnus obesus*, the dark muscle of *Thunnus alalunga*, or the dark muscle of *Xiphias gladius* was minced to a thickness of 1 cm. The minced dark muscle was put into a polyethylene bottle with a lid. After the addition of a 3-fold amount of methanol cooled to 0° C. or less, the mixture was allowed to stand at 0° C. for 1 week or more.

An equal amount of 100% ethanol (cooled to −40° C. or less) was added to 1 l of the methanol extract from which the meat had been removed, and the precipitate was removed by centrifugation (6000×g, 20 min). The remaining extract was evaporated to dryness using a rotary evaporator to obtain a selenium concentrate (1).

After the addition of an adequate amount (about 100 to 500 ml) of cold methanol to the selenium concentrate (1), the mixture was sufficiently stirred, and filtered (filter paper No. 3 manufactured by Toyo Roshi Co., Ltd.; hereinafter the same). The amount of cold methanol may be appropriately determined since the mixture is evaporated after extraction. In this example, cold methanol was added so that a suspension state that allows filtration and extraction was achieved while visually observing that a pigment was extracted.

After the addition of an equal amount of cold ethanol to the extract, the mixture was evaporated using a rotary evaporator to obtain a selenium concentrate (2). After the addition of 10 to 100 ml of cold ethanol to the selenium concentrate (2), the mixture was sufficiently shaken. The precipitate was then removed by filtration or centrifugation (6000×g, 20 min). The extract was collected into a recovery flask, and evaporated using a rotary evaporator to obtain a selenium concentrate (3). The selenium concentrate (3) was dissolved in about 10 ml of cold water, and the precipitate was removed by centrifugation (10,000×g, 5 min).

The color of the selenium concentrate (3) thus obtained was orange, red, or brown. The selenium concentrate (3) was collected as a heme iron complex of the selenium-containing compound. The color of the heme iron complex of the selenium-containing compound differed depending on the type of the sample, the fish species, the pigment content, the storage state (degree of oxidation) of the sample, the extraction temperature, the effect of the reducing agent, and the like.

The selenium content in a dried product obtained by evaporating the selenium concentrate (3) to dryness using a centrifugal evaporator was 16 to 152 mg/kg (dark muscle of *Thunnus orientalis*: 16 mg, dark muscle of *Thunnus maccoyii*: 17 mg, dark muscle of *Thunnus obesus*: 152 mg, dark muscle of *Thunnus alalunga*: 63 mg, and dark muscle of *Xiphias gladius*: 21 mg). The main selenium-containing compounds included in the selenium concentrate (3) were selenoketone-type selenium-containing compounds (chemical formula 3) in which heme iron was bonded to selenium.

Step 2: Removal of Heme Iron

The heme iron complex of the selenium-containing compound included in the selenium concentrate (3) obtained by the step 1 was reduced using a reducing agent to remove heme iron. The yield of the selenium-containing compound was thus increased.

Specifically, dithiothreitol (final concentration: 0.1%) was added to the selenium concentrate (3) derived from the dark muscle of *Thunnus obesus* obtained by the step 1 to obtain a reaction solution. A 5-fold amount of acetonitrile-diethyl ether mixture (volume ratio: 5:1) was added to the reaction solution, and an organic layer including the selenium-containing compound was collected via a two-phase separation. The extraction step and the concentration step were repeated several times until the extract became transparent and clear to remove heme iron, and impurities including coexisting amino acids and ergothioneine were removed as a precipitate to obtain a selenium concentrate (4) including 2240 μg of selenium-containing compounds. The selenium content in the selenium concentrate (4) measured by fluorometry was 4.5 μg/ml (2240 μg/kg).

Step 3: Purification of Selenium-Containing Compound by HPLC

1) HPLC

The selenium concentrate (4) obtained by the step 2 was added to a gel-filtration column ("Ultrahydrogel 120" manufactured by Waters Co., inner diameter: 7.8 mm, column length: 300 mm) that was equilibrated with a 0.1 M acetic acid aqueous solution including 30% of acetonitrile, passed through the column at a flow rate of 2 ml/min to isolate the selenium-containing compound, and eluted at a retention time of 4 to 8 minutes (FIG. 1A).

The eluate was evaporated using a centrifugal evaporator ("VR-1" manufactured by Sakuma Seisakusho Co., Ltd.), added to a C18 reversed-phase column ("Atlantis dC18 column" manufactured by Waters Co., inner diameter: 4.6 mm, column length: 250 mm), and passed through the column at a flow rate of 1 ml/min using 0.1% acetic acid as the mobile phase. A selenium-containing component eluted when 1 to 6 minutes had elapsed after the start of purification, was collected. The selenium content in the eluate was 5000 μg/g (FIG. 1B). Ergothioneine was also present in the eluate.

The eluate was added to a gel-filtration column ("Ultrahydrogel 120" manufactured by Waters Co., inner diameter: 7.8 mm, column length: 300 mm) that was equilibrated with a 0.1 M acetic acid aqueous solution including 30% of acetonitrile, and passed through the column at a flow rate of 2 ml/min to isolate the selenium-containing compound included in the selenium-containing component. Selenium was directly measured by fluorometry or ICP-MS (inductively coupled plasma-mass spectrometry), and a fraction having a high selenium content was collected. The selenium-containing compound was eluted at a retention time of 4 to 8 minutes (FIG. 1C). The above chromatography operation was repeated twice to purify the selenium-containing compound. FIG. 1 shows a case where the dark muscle of *Thunnus obesus* was used as the sample.

The selenium content was determined by fluorometry using 0.005 ml of the purified selenium-containing compound (sample) (dark muscle of *Thunnus orientalis*: 5.5 μg/ml, dark muscle of *Thunnus maccoyii*: 1.3 μg/ml, dark muscle of *Thunnus obesus*: 0.4 μg/ml, and dark muscle of *Xiphias gladius*: 129 μg/ml).

2) ICP-MS 0.1 M ammonium formate was passed through an apparatus connected to an HPLC pump ("Pu712" manufactured by GL Sciences Inc. Ltd.), a sample injector ("9725i" manufactured by Rheodyne), and an ICP-mass spectrometer ("ELAN DRCII" manufactured by Perkin-Elmer) at a flow rate of 0.5 to 1 ml. 2.5 μl of the HPLC fractions isolated in 1) were sequentially injected at intervals of 15 seconds while monitoring selenium-82 (natural isotope of selenium) (0.4 seconds per atomic mass unit). The selenium count increased momentarily only when the sample flowed, and immediately returned to the level before injection. Since the peak level increases depending on the selenium content, a chromatogram of selenium purified by HPLC was obtained off-line. A fraction having a selenium peak of 1,000,000 cps or more was collected.

ICP-MS Measurement Conditions

Figure 3:
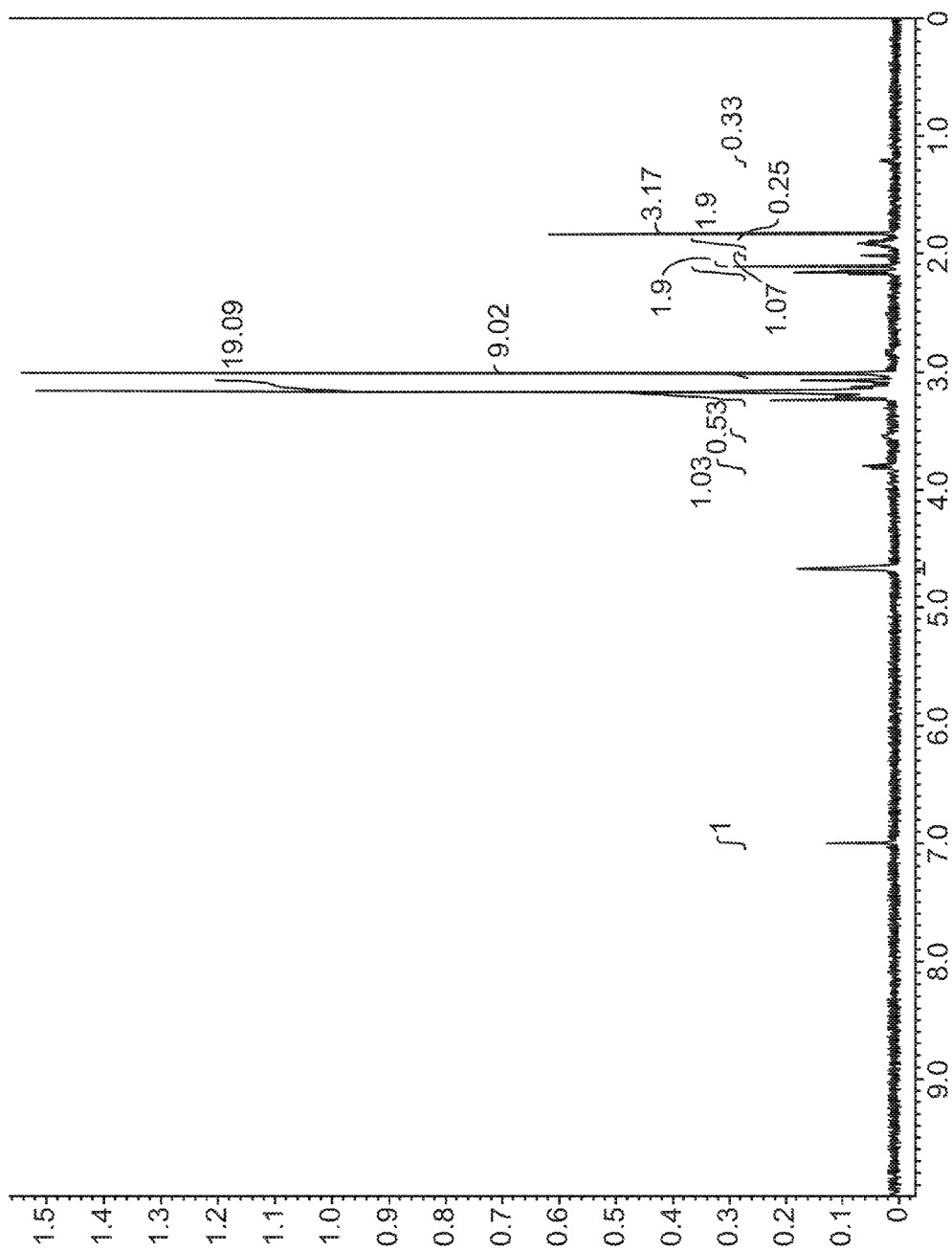
FIG. 3 is a view showing the $^1$H NMR analysis results for a selenium-containing compound (Example 4).

Scans/reading: 1, readings/replicate: 800, replicates/measurement: 1, resident time per mass number: 0.4 sec Step 4: Analysis of Chemical Structure of Selenium-Containing Compound The selenium-containing compound obtained from the dark muscle of *Thunnus orientalis* and purified in the step 3 was subjected to electrospray ionization-mass spectrometry (ESI-MS) using a proton nuclear magnetic resonance analyzer ($^1$H NMR), a quadrupole mass spectrometer ("Quattro II" manufactured by Micromass), and a precision mass spectrometer ("MS700" manufactured by JEOL Ltd.) to analyze the chemical structures of the main selenium-containing compounds included in the tissues. FIG. 3 shows a 500 MHz $^1$H NMR ("ECA500" manufactured by JEOL Ltd.) spectrum. Signals of saturated hydrogen were observed at δ3.08 (d, J=3.4 Hz, 2H), δ3.16 (s, 9H), and δ3.80 (dd, J=3.7, 11.2 Hz, 1H) in deuterated water. These signals agree well with methylene hydrogen at position 3 (δ3.10 (m, 2H)), a methyl group (δ3.19 (s, 9H)), and methine hydrogen at position 2 (δ3.80 (dd, J=4.56, 10.98 Hz, 1H)) of ergothioneine (J. Xu and J. C. Yadan, Synthesis of L-(+)-Ergothioneine, J. Org. Chem., 60, 6296 to 6301 (1995)). The aromatic-ring hydrogen at position 4 of the pyrimidine ring was observed at δ7.00 (s, 1H). Specifically, the signal shifted to the low-field side by 0.3 ppm from the value 6.70 (s, 1H) disclosed in the literature (J. Xu and J. C. Yadan, Synthesis of L-(+)-Ergothioneine, J. Org. Chem., 60, 6296 to 6301 (1995)). Therefore, it was confirmed that the sulfur atom of ergothioneine had been substituted by a selenium atom.

A molecular ion peak at which one hydrogen ion was added to the structure shown by the chemical formula 1 was observed by quadrupole mass spectrometry, and an isotope pattern characteristic of a molecule containing one selenium atom was observed (Table 1). A molecular ion peak indicative of two selenium atoms was observed by accurate mass analysis around a mass number of 553.056 (Table 1). The chemical formula estimated from the mass number was $C_{18}H_{28}N_6O_4Se_2+H^+$. The molecular weight and the isotope distribution theoretically calculated from the atomic weight and the natural isotope abundance ratio of each element agreed well with the observed values.

Figure 2:
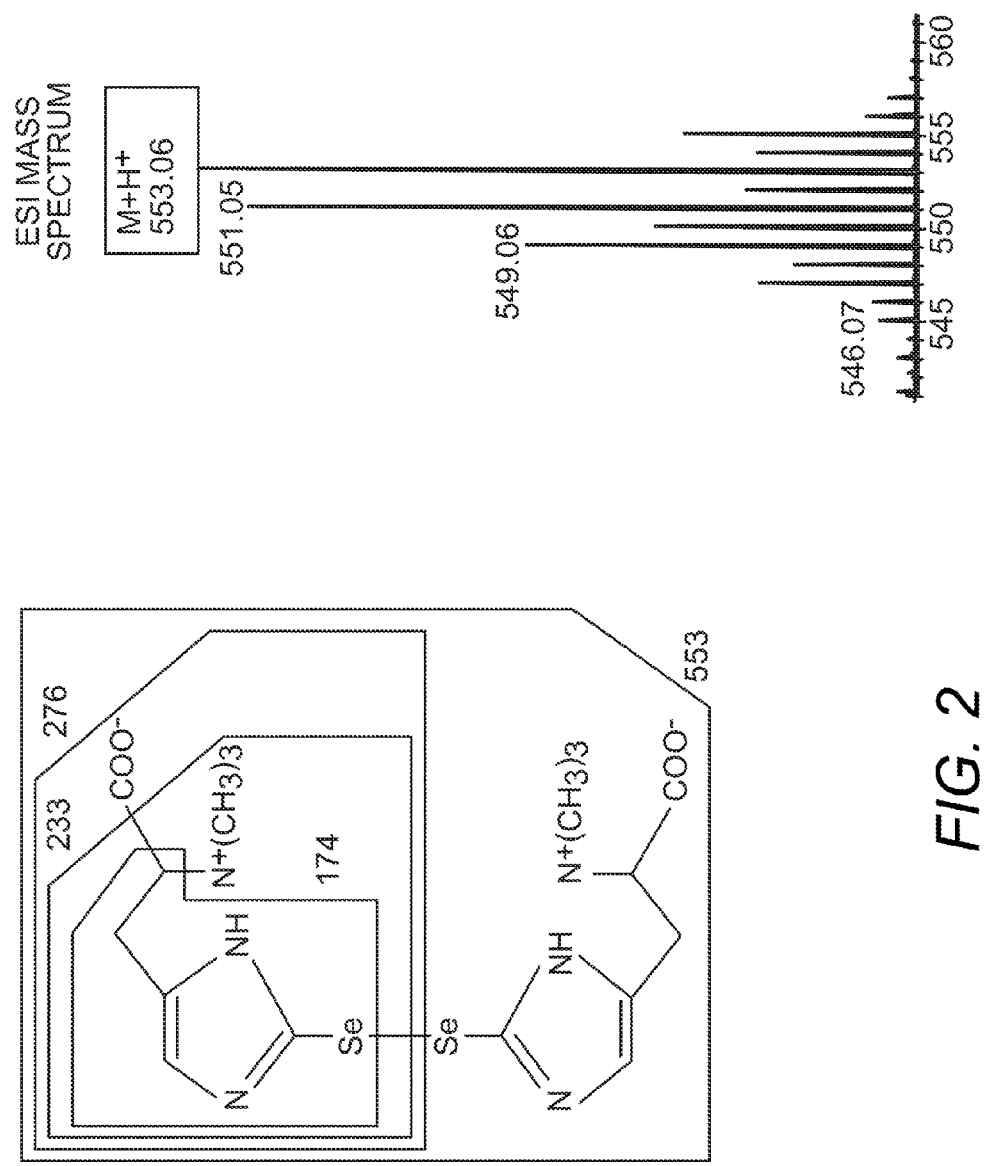
FIG. 2 is a view showing isolation of a selenium-containing compound by gel-filtration chromatography and the chemical structure analysis results for the novel selenium-containing compound (Example 1).

Table 2 shows the fragment ion composition determined by MS/MS analysis. It was estimated from the fragment ion composition that the resulting selenium-containing compound was a dimer (chemical formula 4: oxidized dimer) having a diselenide structure including two selenium atoms, a pyrimidine ring bonded to selenium, a trimethylammonium group, and a carboxyl group (see FIG. 2).

TABLE 1

Mass spectrometry of selenium-containing compound (relative peak value)

| m/z theoretical value (ion valence) | Detected ion Accurate mass analysis |
|---|---|
| 553.0584 | 553.0562 |
| 551.0594 | 551.0543 |
| 549.0607 | 549.0577 |
| 550.0620 | 550.0588 |
| 555.0587 | 555.0540 |
| 552.0619 | 552.0627 |
| 554.0611 | 554.0626 |
| 547.0625 | 547.0573 |
| 548.0630 | 548.0602 |

TABLE 2

Analysis of fragment ion by MS/MS

| Detected ion | Molecular formula |
|---|---|
| 553.0562 | $C_{18}H_{29}N_6O_4Se_2$ |
| 233.0422 | $C_8H_{15}N_3Se$ |
| 173.9692 | $C_5H_6N_2Se$ |
| 79.9165 | Se |
| 59.0730 | $C_3H_9N$ |

4. Physico-Chemical Properties of Selenium-Containing Compound

Table 3 shows property values of the above selenium-containing compound (chemical formula 4: oxidized dimer). Table 3 shows the UV absorption (absorption maximum: 260 nm) and fluorescence (maximum excitation wavelength: 240 nm, 280 nm, and 338 nm, maximum fluorescence wavelength: 405 nm). A monomer was obtained by reducing the selenium-containing compound using 10 mM dithiothreitol, and had a molecular weight of m/z=278.0 (see Table 3). Therefore, it was confirmed that the selenium-containing compound was a dimer (chemical formula 4: oxidized dimer) in which the individual selenium-containing compounds are bonded through a diselenide bond.

The monomer was a novel selenium-containing compound (chemical formula 2) having a chemical structure in which the sulfur atom of the thiol group of ergothioneine was substituted by a selenium atom. Since the novel selenium-containing compound had a chemical structure similar to that of ergothioneine, the novel selenium-containing compound was named "selenoneine".

TABLE 3

Physico-chemical properties of selenium-containing compound (chemical formula 4)

| Item | Properties |
|---|---|
| $^1$H NMR (D$_2$O) | δ3.08 (d, J = 3.4 Hz, 2H), δ3.16 (s, 9H), δ3.80 (dd, J = 3.7, 11.2 Hz, 1H), δ7.00 (s, 1H) |
| Molecular weight (M + H)$^+$ | Monomer: m/z = 278.0, dimer: m/z = 553.06 |
| Fluorescence | Maximum excitation/fluorescence wavelength 240/405 nm (molar fluorescence coefficient: 0.823 × 10$^3$ cm$^{-1}$ · mol$^{-1}$) 280/405 nm (molar fluorescence coefficient: 1.51 × 10$^3$ cm$^{-1}$ · mol$^{-1}$) 337/405 nm (molar fluorescence coefficient: 1.46 × 10$^3$ cm$^{-1}$ · mol$^{-1}$) |
| UV absorption | Maximum absorption wavelength: 260 nm (molar fluorescence coefficient: 525 cm$^{-1}$ · mol$^{-1}$) |
| Color | Yellow |
| Solubility | Soluble in water, ethanol, and methanol; scarcely soluble in acetone and acetonitrile |

2) Extraction of Selenium-Containing Compound from Whale Meat 350 g of the lean meat (selenium content: 0.91 mg/kg) of *Globicephala macrorhyncus* was minced to dimensions of 1×1×1 cm or less. The minced lean meat was put into a polyethylene bottle with a lid. After the addition of a 4-fold amount of methanol cooled to 0° C. or less, the mixture was allowed to stand at 0° C. for 1 month or more. The selenium content in the lean meat of *Globicephala macrorhyncus* was obtained by decomposing 0.1 g of the lean meat using a mixed acid, and determining the selenium content by fluorometry.

1 l of the ethanol extract from which the meat had been removed was evaporated to dryness using a rotary evaporator to obtain a selenium concentrate (1) including a heme iron complex of a selenium-containing compound (chemical formula 3).

After the addition of 100 ml of a 0.1% glutathione (reduced form) aqueous solution to the selenium concentrate (1), the mixture was stirred at room temperature for 12 hours. After the addition of 400 ml of cold ethanol, the mixture was filtered to remove heme iron. The extract was evaporated using a rotary evaporator to obtain a selenium concentrate (2).

The selenium concentrate (2) was dissolved in 10 ml of cold water. After the addition of 50 ml of cold ethanol, the precipitate was removed by filtration. The extract was collected into a recovery flask, and evaporated using a rotary evaporator to obtain a selenium concentrate (3) including a selenium-containing compound (chemical formula 4: oxidized dimer).

The selenium concentrate (3) was dissolved in 10 ml of cold water. The selenium content in the selenium concentrate (3) thus obtained from the whale meat was measured by fluorometry. The yield of selenium was found to be 92 µg.

3) Extraction of Selenium-Containing Compound from Tuna Blood

Extraction Example 1

The blood (selenium content: 29.8 mg/l) of *Thunnus orientalis* was hemolyzed by adding a 5-fold amount of cold water, and centrifuged (6000×g, 10 min). The supernatant liquid was collected, and evaporated to obtain a selenium concentrate (1). The selenium content in a dried product obtained by evaporating the selenium concentrate (1) to dryness using a centrifugal evaporator was 111 mg/kg.

Extraction Example 2

A 5-fold amount of cold ethanol was added to 100 ml of the blood (selenium content: 34.7 mg/l) of *Thunnus orientalis*, and the solid was ground using a POLYTRON™ homogenizer. The selenium content in the blood of *Thunnus orientalis* was obtained by decomposing 0.01 ml of the blood using a mixed acid, and determining the selenium content by fluorometry. After removing the precipitate by centrifugation (6000×g, 20 min), the remaining mixture was evaporated to dryness using a rotary evaporator to obtain a selenium concentrate (1) including a heme iron complex of a selenium-containing compound (chemical formula 3).

The selenium concentrate (1) was dissolved in 50 ml of cold water. After the addition of 300 ml of cold acetonitrile (for large quantity preparative liquid chromatography) (manufactured by Kanto Kagaku Co., Ltd., 99.8%, cooled to 0° C. or less), the mixture was stirred, and then allowed to stand. The upper acetonitrile layer was collected via a two-phase separation to obtain a selenium concentrate (2) including a selenium-containing compound (chemical formula 4: oxidized dimer). Heme iron was removed from the selenium-containing compound by extraction with acetonitrile. The selenium content in a dried product obtained by evaporating the selenium concentrate (2) obtained from the blood of *Thunnus orientalis* to dryness using a centrifugal evaporator was 3100 mg/kg.

Extraction Example 3

0.3 g of a dithiothreitol powder (manufactured by Nacalai Tesque, Inc.) was added to 300 ml of the blood of *Thunnus orientalis* aimed at isolating a selenium-containing compound from heme iron. The selenium content in the blood of *Thunnus orientalis* was obtained by decomposing 0.01 ml of the blood using a mixed acid, and determining the selenium content by fluorometry.

After the addition of 300 ml of a mixed solvent of tetrahydrofuran (manufactured by Wako Pure Chemical Industries, Ltd.) and dichloromethane (manufactured by Wako Pure Chemical Industries, Ltd.) (1:1), the mixture was gently mixed. After the addition of 300 ml of dichloromethane, the mixture was gently mixed again. The lower organic solvent layer was collected, and evaporated using a rotary evaporator to obtain a selenium concentrate (1) including a selenium-containing compound (chemical formula 4: oxidized dimer).

The selenium concentrate (1) was dissolved in 15 ml of cold water, and the precipitate was removed by centrifugation (6000×g, 20 min). The selenium content in the selenium concentrate (1) was 66 mg/l.

4) Extraction of Selenium-Containing Compound from Hepatopancreas of *Thunnus orientalis*

100 g of the hepatopancreas (selenium content: 8.1 mg/kg, mercury content: 3.9 mg/kg) of *Thunnus orientalis* was cut to a thickness of 5 mm or less, and put into a polyethylene bottle with a lid. After the addition of a 2-fold amount of ethanol cooled to 0° C. or less, the mixture was allowed to stand at 0° C. for 1 month or more. The ethanol extract from which the solids had been removed by filtration was evaporated to dryness using a rotary evaporator to obtain a selenium concentrate (1) including a heme iron complex of a selenium-containing compound (chemical formula 3).

The selenium content in the hepatopancreas of *Thunnus orientalis* was obtained by decomposing 0.2 g of the hepatopancreas using a mixed acid, and determining the selenium content by fluorometry. The mercury content was determined by cold vapor atomic absorption spectrometry.

The selenium concentrate (1) was dissolved in 20 ml of cold water. After the addition of 200 ml of cold acetonitrile (manufactured by Wako Pure Chemical Industries, Ltd.), the mixture was stirred, and then allowed to stand. The upper acetonitrile layer was collected via a two-phase separation to obtain a selenium concentrate (2) including a selenium-containing compound (chemical formula 4: oxidized dimer). Heme iron was removed from the selenium-containing compound by extraction with acetonitrile. The selenium concentrate (2) thus obtained from the hepatopancreas of *Thunnus orientalis* was evaporated using a rotary evaporator, and dissolved in a small quantity of water to obtain 1 ml of a crude selenium extract.

The crude selenium extract was wet-decomposed using a mixed acid, and the selenium content (fluorometry), the iron content (ICP emission spectrometry), the mercury content (cold vapor atomic absorption spectrometry), and the nitrogen content (Kjeldahl method) were analyzed. The acetonitrile soluble extract had a selenium content of 50 mg/kg, an iron content of 1.8 mg/kg, a mercury content of 0.012 mg/kg, and a nitrogen content of 45,900 mg/kg. The acetonitrile insoluble extract had a selenium content of 12 mg/kg, an iron content of 103 mg/kg, a mercury content of 0.001 mg/kg, and a nitrogen content of 168,000 mg/kg.

It was thus confirmed that the mercury content decreases to 1/300th of that of the hepatopancreas (i.e., an organ having a mercury content several times that of muscle) by extraction of selenium. Since the selenium concentrate contains a large amount of nitrogen and iron (i.e., nutrient elements), the selenium concentrate can be safely and effectively used as a feed additive and the like.

5) Extraction of Selenium-Containing Compound from Dark Muscle of *Thunnus maccoyii*

500 ml of cold water was added to 100 g of the dark muscle of *Thunnus maccoyii*, and the solid was ground using a POLYTRON™ homogenizer. The precipitate was removed by centrifugation (6000×g, 20 min) to obtain a water extract (1).

After the addition of 2-mercaptoethanol (final concentration: 10 mM) or dithiothreitol (final concentration: 50 mM) to 100 ml of the water extract (1), the mixture was stored at room temperature for 1 hour (reduction process) to obtain an extract (2). 20 ml of the water extract (1) was heated in a boiling water bath to obtain a hot water extract (2). The pH of the water extract (1) was adjusted to 3 by adding 1 M hydrochloric acid, and allowed to stand at room temperature for 10 minutes to obtain an acid extract (2).

After the addition of 400 ml of cold ethanol to each extract (2), solids were removed by centrifugation (6000×g, 20 min). The residue was evaporated using a rotary evaporator to obtain a selenium concentrate (1). After the addition of acetonitrile to the selenium concentrate (1), the mixture was stirred, and then allowed to stand. The upper acetonitrile layer was collected via a two-phase separation, evaporated using a rotary evaporator, and dissolved in a small quantity of water to obtain a crude selenium extract including a selenium-containing compound (chemical formula 4: oxidized dimer).

The crude selenium extract was wet-decomposed using a mixed acid, and the selenium content (fluorometry), the iron content (ICP emission spectrometry), and the mercury content (cold vapor atomic absorption spectrometry) were analyzed. Table 4 shows the selenium content, the iron content, and the mercury content in each crude selenium extract.

TABLE 4

| | Se (μg) | Fe (μg) | Hg (μg) |
|---|---|---|---|
| No additive | 3.8 | 14 | 0.009 |
| DTT (50 mM) | 4.7 | 201 | 0.700 |
| Mercaptoethanol (10 mM) | 1.4 | 15 | 0.032 |
| Hot water | 2.4 | 33 | <0.001 |
| Hydrochloric acid (pH: 3.0) | 5.0 | 21 | 0.125 |

Example 2

Production of Selenol-Type Selenium-Containing Compound or Selenoketone-Type Selenium-Containing Compound The selenoketone-type selenium-containing compound of Example 1 (chemical formula 3) was subjected to selenoketone-selenol tautomeric conversion to obtain a selenol-type selenium-containing compound (chemical formula 2).

The selenium-containing compound according to one embodiment of the invention has a molecular structure in which a selenol group is bonded to a carbon atom at position 2 of a pyrimidine ring. A selenol group forms a tautomer that is in an equilibrium state with a selenoketone group. The selenoketone group and the selenol group are functional groups that are unstable to heat and oxygen. The selenoketone group liberates a low-molecular-weight selenium compound, and rapidly loses selenium. On the other hand, the selenol group easily produces a relatively stable dimer (oxidized dimer) in a gas phase or a non-polar solvent (e.g., cyclohexane or tetrahydrofuran) in which the equilibrium shifts to the selenol isomer (J. Elguero, C. Marzin, A. R. Katritzky, and P. Linda, "The Tautomerism of Heterocycles", A. R. Katritzky and A. J. Boulton Eds.; Advances in Heterocyclic Chemistry, Supplement No. 1; Academic Press: New York, 1976).

A 2-fold amount of a mixed solvent of tetrahydrofuran and cyclohexane (1:1) was added to a selenium concentrate including a selenium-containing compound (chemical formula 3), and the mixture was stirred at room temperature overnight to obtain an emulsion. The emulsion was evaporated using a rotary evaporator. After extracting the selenium-containing compound with purified water, water was removed using a centrifugal evaporator to collect a selenium concentrate (5) including a yellow oily selenol-type selenium-containing compound (chemical formula 2). The selenium content in the selenium concentrate (5) was 2400 mg/kg.

Example 3

Optimization of Selenium-Containing Compound Extraction Conditions

1. Study of Extraction Solvent

The selenium-containing compound extraction conditions were optimized by extracting a selenium-containing compound using a different extraction solvent, and comparing the yields of the selenium-containing compound. The internal organ of *Beryx splendens* was used as the sample, and ethanol, methanol, or acetone was used as the extraction solvent.

80% cold ethanol, cold methanol (cooled to −40° C. or less), or acetone was added to 20 g of the internal organ of *Beryx splendens* as the extraction solvent, and the solid was ground using a POLYTRON™ homogenizer. After removing the precipitate by centrifugation (6000×g, 20 min), the mixture was evaporated using a rotary evaporator to obtain a selenium concentrate (1) including a heme iron complex of a selenium-containing compound (chemical formula 3).

After the addition of 200 ml of acetonitrile to the selenium concentrate (1), the mixture was stirred, and then allowed to stand. The upper acetonitrile layer was collected via a two-phase separation to obtain a selenium concentrate (2) including a selenium-containing compound (chemical formula 4: oxidized dimer). The selenium concentrate (2) thus obtained was evaporated using a rotary evaporator, and dissolved in a small quantity of water to obtain 12 ml of a methanol extract, 14 ml of a 80% ethanol extract, or 8 ml of an acetone extract (i.e., crude selenium extract).

The crude selenium extract was wet-decomposed using a mixed acid, and the selenium content, the iron content (ICP emission spectrometry), and the mercury content (cold vapor atomic absorption spectrometry) were analyzed.

When using methanol as the extraction solvent, the selenium content and the mercury content in the extract were 8.9 mg/l and 0.046 mg/l, respectively. When using 80% ethanol as the extraction solvent, the selenium content and the mercury content in the extract were 4.5 mg/l and 0.008 mg/l, respectively. When using acetone as the extraction solvent, the selenium content and the mercury content in the extract were 5.6 mg/l and 0.010 mg/l, respectively. It was thus confirmed that a selenium concentrate including a selenium-containing compound at a high concentration can be obtained using each of the above extraction solvents.

2. Purification of Selenium-Containing Compound Using Ion-Exchange Resin Column

The purity of a selenium concentrate including a selenium-containing compound was increased by removing impurities by purification using an ion-exchange resin column.

Specifically, 100 g of the dark muscle of *Thunnus orientalis* was minced to dimensions of 1×1×1 cm or less. After the addition of a 10-fold amount of cold ethanol, the dark muscle was ground using a POLYTRON™ homogenizer, and centrifuged (6000×g, 20 min). The supernatant liquid was collected, and evaporated using a rotary evaporator to obtain a selenium concentrate (1) including a heme iron complex of a selenium-containing compound (chemical formula 3).

The selenium concentrate (1) was dissolved in 100 ml of cold methanol, and filtered. The extract was evaporated using a rotary evaporator to obtain a selenium concentrate (2). Cold water was added to the selenium concentrate (2) so that the liquid volume was 30 ml.

The selenium concentrate (2) to which cold water was added, was added to a Sep-Pack Accell Plus QMA anion-exchange column (manufactured by Waters Co., internal volume: 50 mg) that was equilibrated with water. After washing the column with 20 ml of water, 10 ml of a 0.1% acetic acid aqueous solution was added to the column to elute a selenium concentrate (3) including a selenium-containing compound. The selenium content in the selenium concentrate (3) including a selenium-containing compound was 5.8 μg/ml.

Example 4

Production and Analysis (Mass Spectrometry) of Analog of Selenium-Containing Compound In order to analyze the chemical structure and the reactivity of a selenium-containing compound produced in vivo and in vitro, the selenium-containing compound (chemical formula 4: oxidized dimer) included in the selenium concentrate (extracted from the dark muscle of *Thunnus orientalis*) prepared in Example 1 was reduced and carboxymethylated (Masatsune Ishiguro, Chemical modification of SH group, Biochemistry Experimental Method 8, Japan Scientific Societies Press (1978)) to obtain a chemically modified reaction product (analog of selenium-containing compound). The reaction product was identified by mass spectrometry.

Specifically, the selenium-containing compound was reduced using dithiothreitol in accordance with the cystine reduction and carboxymethylation method, followed by the addition of iodoacetic acid to obtain a reaction product. The reaction product was purified using a gel-filtration column ("Ultrahydrogel 120" manufactured by Waters Co., inner diameter: 7.8 mm, column length: 300 mm) that was equilibrated with 1 M ammonium acetate including 30% of acetonitrile to obtain a component having UV absorption at 260 nm as a chemically modified reaction product (analog of selenium-containing compound).

Figure 4:
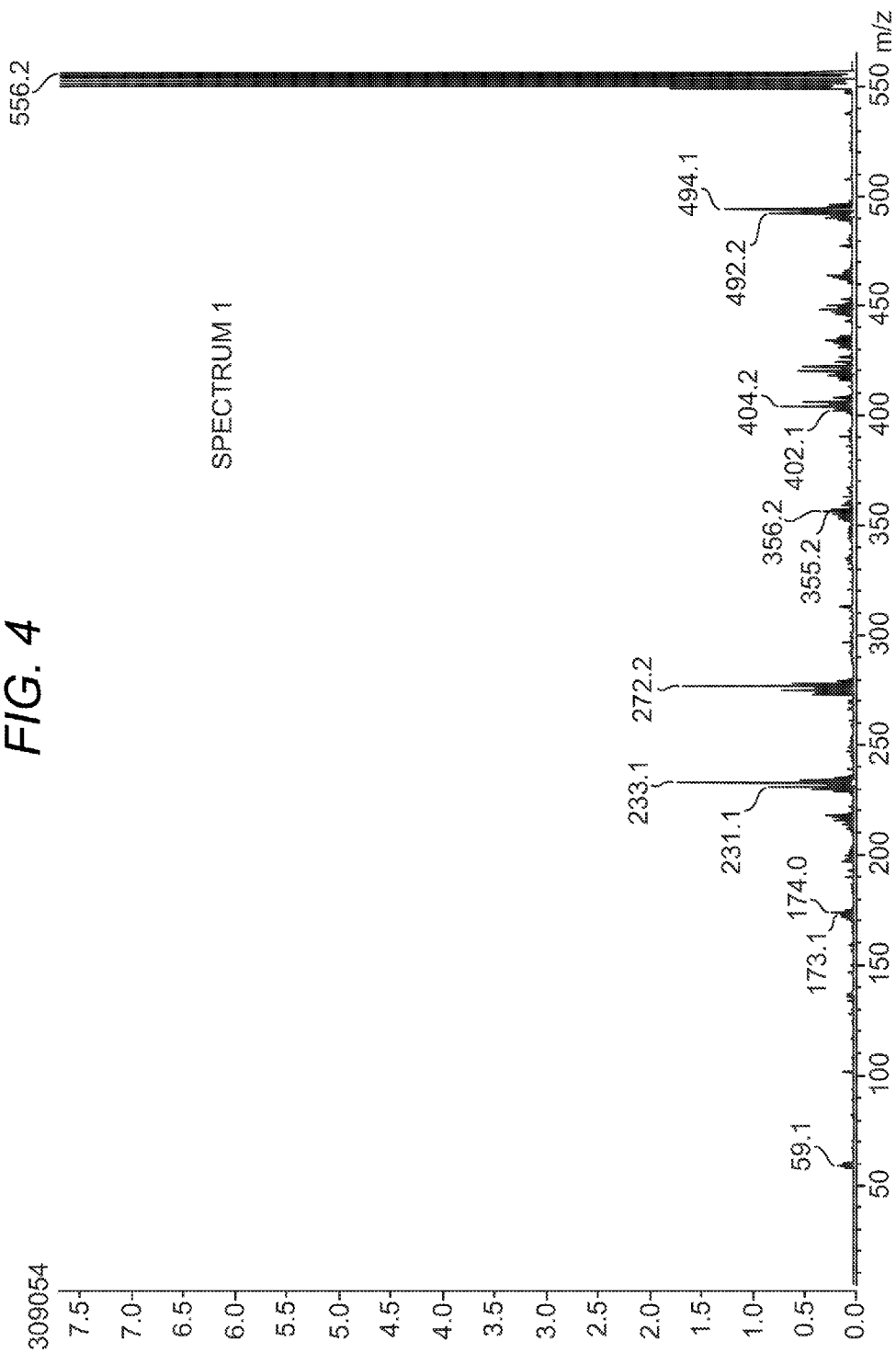
FIG. 4 is a view showing the electrospray ionization mass spectrometry (ESI-MS, spectrum 1) results and the electrospray ionization tandem mass spectrometric analysis (ESI-MS/MS, spectrum 2) results for a selenium-containing compound oxidized dimer (Example 4).

The chemically modified reaction product (analog of selenium-containing compound) was analyzed (mass spectrometry) within the mass range (m/z) of 100 to 600 using an ESI-MS ("Quattro II" manufactured by Micromass). When analyzing the mass of the product using the ESI-MS, the molecular ions of the oxidized dimer of the selenium-containing compound (m/z=553, 277) and an ergothioneine addition product (m/z=491) were observed, and a product in which the selenol group of the selenium-containing compound monomer was carboxymethylated (ions: m/z=233 (277-$CO_2$) and m/z=174 (277-$CO_2$—$N(CH_3)_3$)) was detected (Table 5 and FIG. 4).

The selenium-containing compound (chemical formula 4: oxidized dimer) was reduced at room temperature for 30 minutes using 10 mM dithiothreitol, and the mass of the product was analyzed using the ESI-MS. A reduced monomer (chemical formula 2) was detected.

It is known that a plurality of selenium isotopes exist. The theoretical mass number of the M+H$^+$ ion of the reduced monomer of the selenium-containing compound based on the selenium isotope abundance ratio is 278.0 (100.0%), 276.0 (49.5%), 274 (18.8%), 280 (18.5%), 275.0 (17.4%), 279.0 (11.1%), 277.0 (5.4%), 281.0 (2.0%), and 272 (1.8%) (the percentage in the parentheses is the theoretical abundance ratio of each ion), and the measured value was 278.0 (100.0%), 276.1 (51.8%), 274 (18.9%), 280 (18.3%), 275.1 (18.9%), 279.1 (11.6%), 277.1 (7.3%), 281.0 (2.4%), and 272 (2.7%). The molecular weight theoretically calculated from the atomic weight and the natural isotope abundance ratio of each element agrees well with the measured values, and a signal distribution in which one molecule contains one selenium atom was obtained.

It was thus confirmed that the main selenium-containing compounds included in the tissues of fish are selenium-containing compound dimers (chemical formula 4: oxidized dimer) in which the individual selenium-containing compounds are bonded through a diselenide bond.

TABLE 5

Identification of analog by chemical modification of selenium-containing compound

| m/z theoretical value (ion valence) | Detected ion | Chemical formula |
|---|---|---|
| 553.1, 551.1, 549.1 (1+ ion), 277 (2+ ion) | 553.1, 551.1, 549.1, 277.25 | Selenoneine dimer |
| 505.1, 503.1, 506.1, 507.1 | 505.4, 503.4, 506.4, 507.4 | Ergothioneine addition product |
| 336.0, 334.0, 332.0, 338.0 | 336.2, 334.2, 332.3, 338.3 | Reduced carboxymethylated product |
| 280.0, 278.0, 276.0, 275.0, 274.0 | 280.1, 278.0, 276.1, 275.1, 274.1 | Reduced monomer |

Example 5

Use of Selenium-Containing Compound

The applicability of a selenium-containing compound (chemical formula 4: oxidized dimer) purified in the same manner as in Example 1 as a quantitative analysis standard substance or a medium additive, an antioxidant, a metmyoglobin formation inhibitor, and the like was determined.

1. Utility of Selenium-Containing Compound as Standard Substance

Whether or not a selenium-containing compound obtained according to the invention can be used as a standard substance for quantitatively analyzing a selenium-containing compound in a sample was determined.

Specifically, the selenium-containing compound (chemical formula 4: oxidized dimer) according to one embodiment of the invention, glutathione peroxidase (SIGMA), a selenium standard solution (selenium dioxide aqueous solution (CAS No. 7446-08-4, manufactured by Wako Pure Chemical Industries, Ltd.), selenocystine (manufactured by SIGMA), or selenomethionine (manufactured by Tokyo Kasei Kogyo Co., Ltd.) was used as the sample, and introduced into an ICP-MS by flow injection or HPLC using a neutral buffer as the mobile phase. Organic selenium included in the sample was detected as a selenium-82 ion by ionization due to argon plasma excitation.

The selenium-82 ion was measured by dissolving the selenium-containing compound (chemical formula 4: oxidized dimer) according to one embodiment of the invention in 0.1 M ammonium formate, and introducing the solution into an inductively coupled plasma mass spectrometer. Glutathione peroxidase, sodium selenite (manufactured by Wako Pure Chemical Industries, Ltd.), selenocystine, and selenomethionine were prepared so that the selenium content was 100 pg/µl. 5 µl, 10 µl, or 20 µl of each sample was introduced, and a signal of selenium-82 was detected using an ICP-MS ("ELAN DRCII" manufactured by Perkin-Elmer). The concentration of the selenium-containing sample was corrected using the selenium content analyzed by fluorometry.

Figure 5:
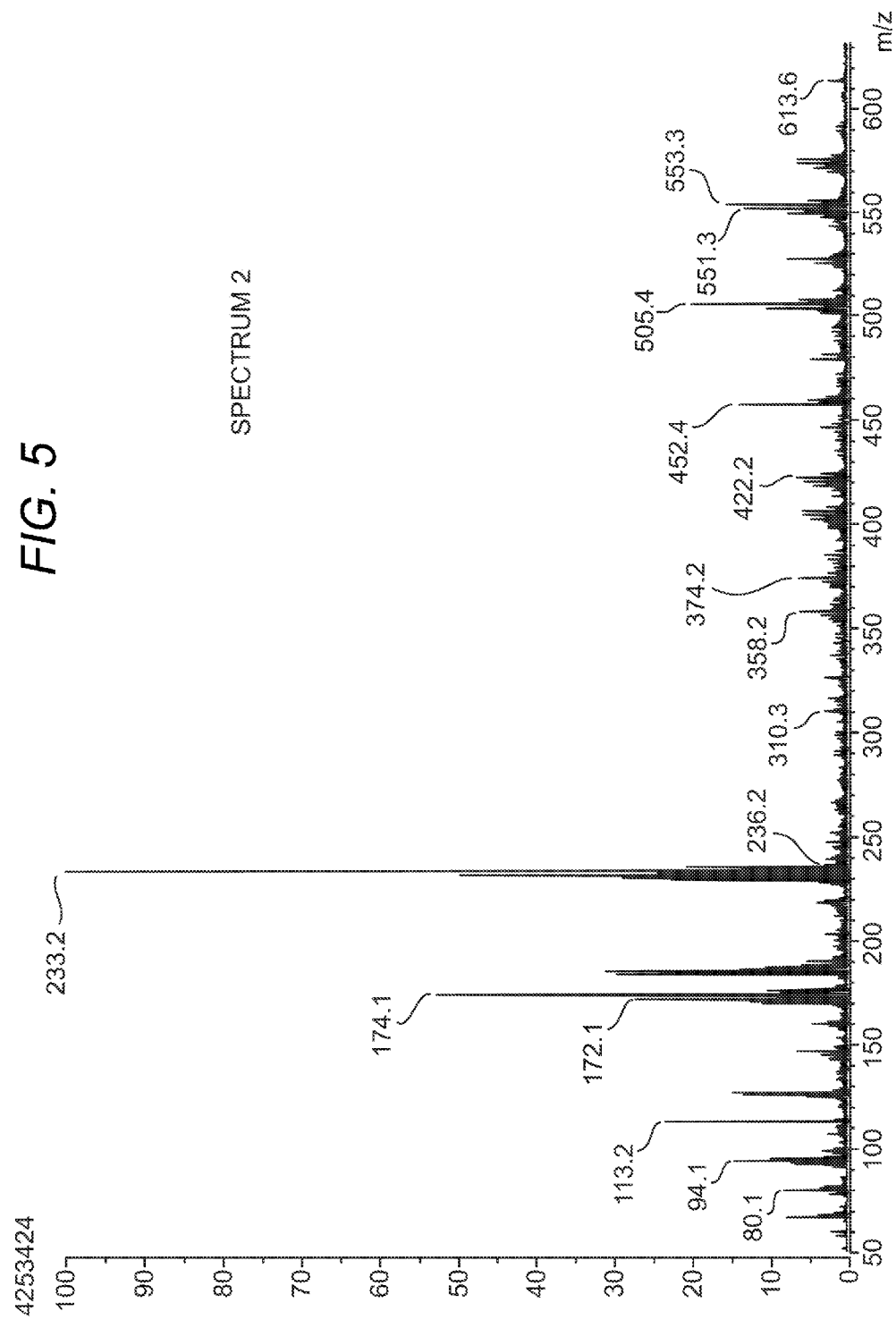
FIG. 5 is a view showing the liquid chromatography-inductively coupled plasma mass spectrometry (HPLC-ICP-MS) results for a selenium-containing compound (Example 5).

As shown in FIG. 5, the selenium-containing compound (chemical formula 4: oxidized dimer) according to one embodiment of the invention and the selenium-containing samples (1: glutathione peroxidase, 2: selenium dioxide aqueous solution, 3: L-selenocystine, 4: L-selenomethionine) were detected at different retention times, and a calibration curve with a correlation coefficient of 0.99 or more was obtained. It was thus confirmed that these substances can be isolated and quantitatively determined (Table 6).

TABLE 6

Analysis of selenium-containing compound and selenium-containing samples by ICP-MS

| | Elution time (min) | Peak area (Se pmol$^{-1}$) |
|---|---|---|
| Glutathione peroxidase | 5.4 | 3492 |
| Selenium dioxide aqueous solution | 7.4 | 5006 |
| Selenocystine | 7.8 | 2954 |
| Selenomethionine | 9.8 | 2789 |
| Selenium-containing compound (chemical formula 4) | 10.5 | 3480 |

2) Use of Selenium-Containing Compound (Chemical Formula 4: Oxidized Dimer) as Standard Substance A selenium-containing compound included in the dark muscle of *Thunnus orientalis*, the ordinary muscle of *Thunnus orientalis*, the blood of *Thunnus orientalis*, the spleen of *Thunnus orientalis*, the liver of *Thunnus orientalis*, the gills of *Thunnus orientalis*, the heart of a chicken, the liver of a chicken, the hepatopancreas of *Todarodes pacificus*, and human blood was quantitatively analyzed in the same manner as in 1) using the selenium-containing compound (chemical formula 4: oxidized dimer) according to one embodiment of the invention as the standard substance.

Specifically, 0.1 g of the dark muscle of *Thunnus orientalis*, the ordinary muscle of *Thunnus orientalis*, the blood of *Thunnus orientalis*, the spleen of *Thunnus orientalis*, the liver of *Thunnus orientalis*, the gill of *Thunnus orientalis*, the heart of a chicken, the liver of a chicken, the hepatopancreas of *Todarodes pacificus*, or human blood was ground using a POLYTRON™ homogenizer (manufactured by Kinematica, Inc.) together with 0.5 ml of Millipore water, and centrifuged at 12,000 rpm for 5 minutes. The supernatant liquid was used as the sample. The sample was filtered (syringe filter No. 6872-1304 manufactured by Whatman, Inc.), 2 to 10-fold diluted with an HPLC mobile phase, and introduced into an HPLC-ICP-MS. A selenium-containing compound contained in the sample was quantitatively analyzed under measurement conditions shown in Table 7.

Figure 6:
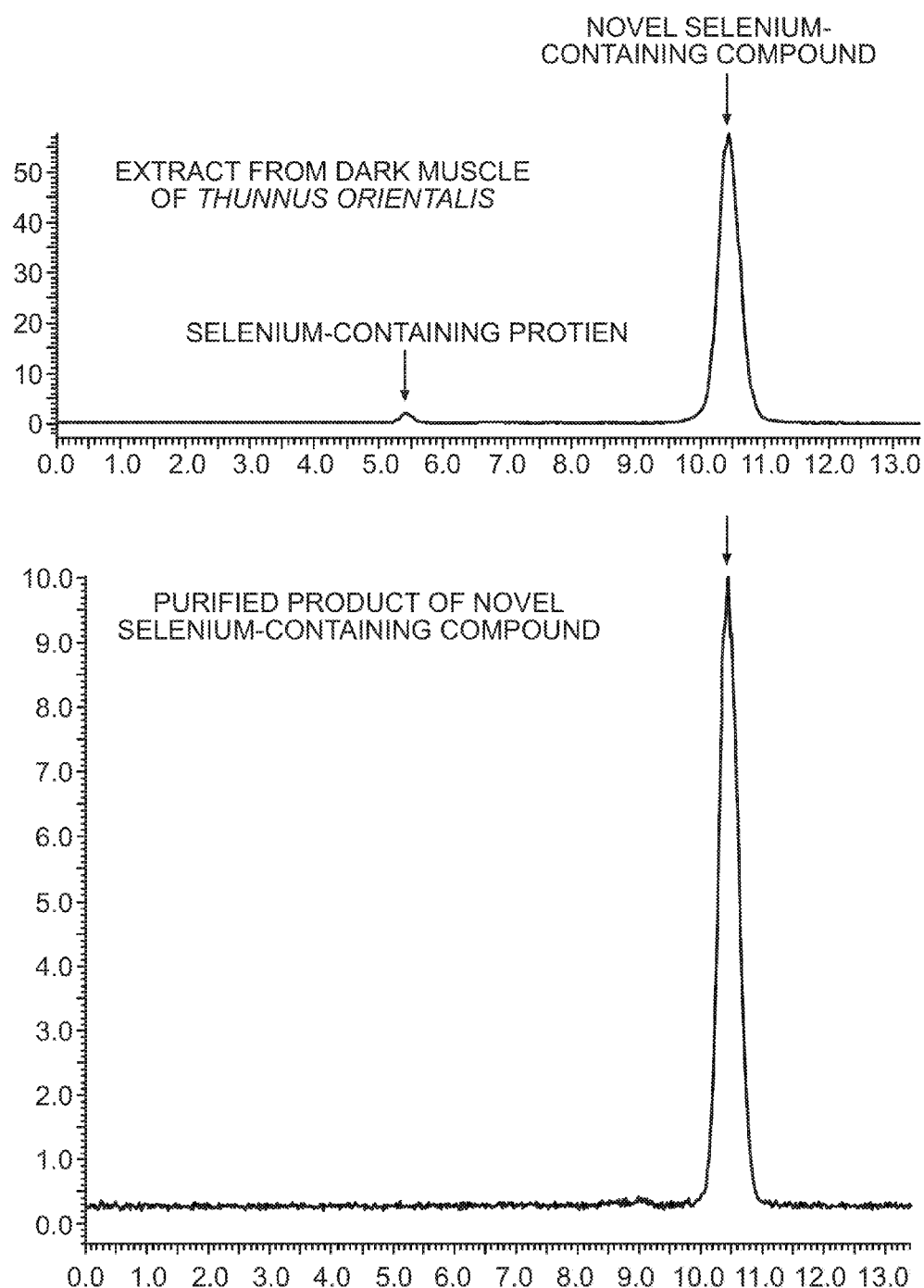
FIG. 6 is a view showing the HPLC-ICP-MS results for a selenium-containing compound (Example 5).

As shown in FIG. 6 and Table 8, it was found that the dark muscle of *Thunnus orientalis* includes the selenium-containing compound (selenium-containing compound having a skeleton shown by the chemical formula 1, hereinafter referred to as "(chemical formula 1)") according to one embodiment of the invention in an amount corresponding to a selenium content of 95%. Specifically, the content of the selenium-containing compound (chemical formula 1) according to one embodiment of the invention was indirectly estimated by indicating the content of selenium-containing compounds other than the selenium-containing compound (chemical formula 1) according to one embodiment of the invention (i.e., compounds that are eluted at a retention time differing from that of the selenium-containing compound (chemical formula 1) according to one embodiment of the invention, and include selenium) with respect to the total selenium content by the area ratio of the peak of selenium-containing compounds other than the selenium-containing compound (chemical formula 1) according to one embodiment of the invention to the total selenium peak.

For example, the ratio of the selenium-containing compound (chemical formula 1) according to one embodiment of the invention included in the dark muscle of *Thunnus orientalis* with respect to the total selenium content was calculated as follows.

$$(100-2.5)*2018.9/(2018.9+44.7)=95.3\%$$

A selenium-containing protein (i.e., a polymer other than selenoprotein P that has a molecular weight of 20,000 or more and contains one selenium atom in the molecule), the selenium-containing compound (chemical formula 1) according to one embodiment of the invention, and selenium-containing compounds other than the selenium-containing compound (chemical formula 1) according to one embodiment of the invention were detected from various tissues. The selenium-containing protein content is indicated by the GPX equivalent amount calculated from Table 7, and the content of selenium-containing compounds other than the selenium-containing compound (chemical formula 1) according to one embodiment of the invention is indicated by the ratio of the area to the detected total peak area.

Figure 7:
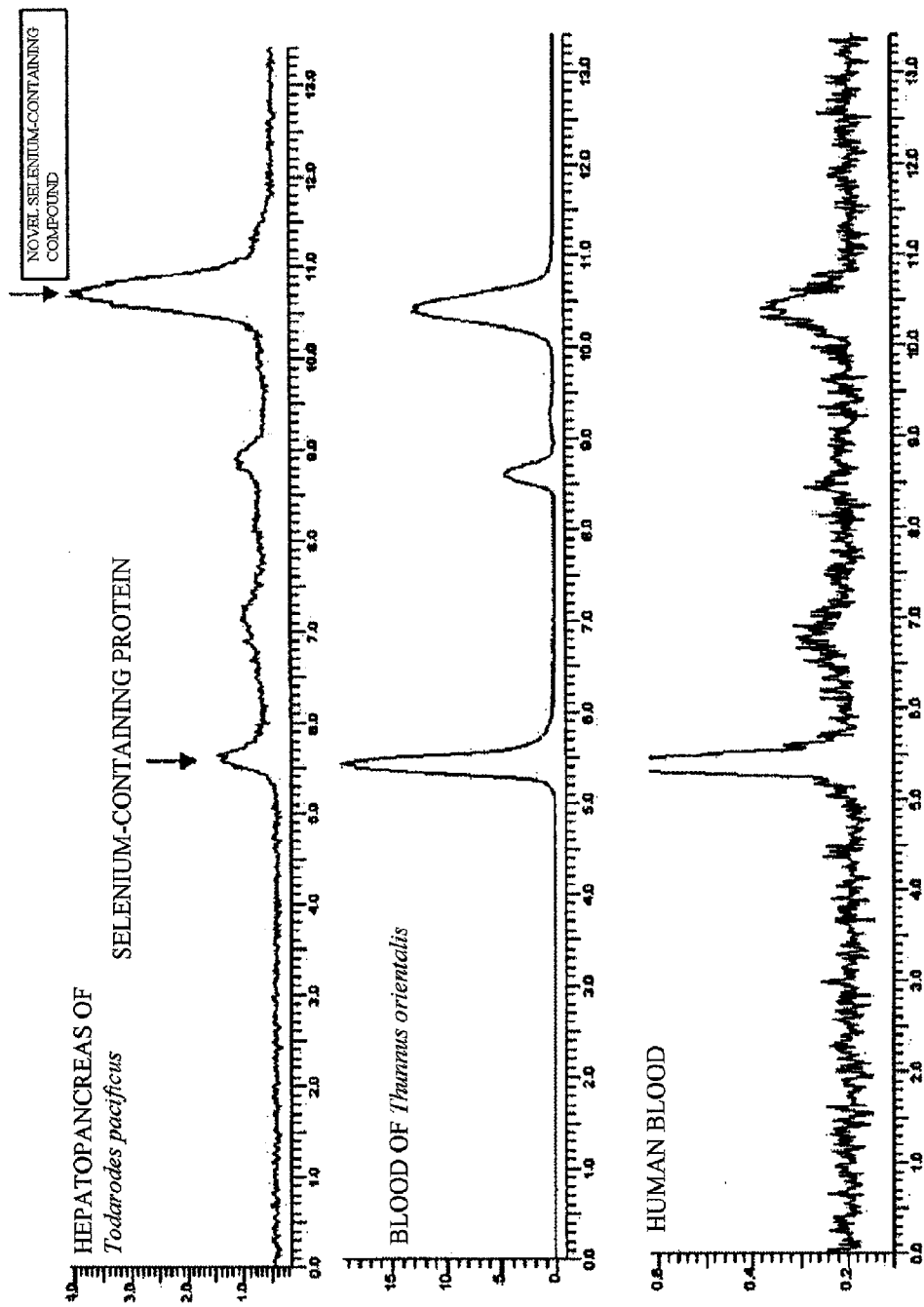
FIG. 7 is a view showing the HPLC-ICP-MS results for a selenium-containing compound (Example 5).

As shown in FIG. 7 and Table 9, it was confirmed that the selenium-containing compound (chemical formula 1) according to one embodiment of the invention was included (distributed) in the ordinary muscle of *Thunnus orientalis*, the blood of *Thunnus orientalis*, the heart of a chicken, the liver of a chicken, the hepatopancreas of *Todarodes pacificus*, and human blood in the same manner as in the dark muscle of *Thunnus orientalis*.

The dark muscle and the ordinary muscle of *Thunnus orientalis* were fractionated into a cytoplasmic fraction (78000×g, supernatant liquid), a microsomal fraction (precipitated at 22500×g to 78000×g), and a mitochondrial fraction (precipitated at 700×g to 8000×g) by centrifugation (Michiaki Yamashita, Studies on cathepsins in the muscle of chum salmon, Bulletin of the National Research Institute of Fisheries Science, 5, 9-114 (1993)), and localization of the selenium-containing compound (chemical formula 1) according to one embodiment of the invention in the cells was analyzed by the method described in Example 3. It was confirmed that the selenium-containing compound (chemical formula 1) according to one embodiment of the invention was localized in cytoplasm together with glutathione peroxidase (i.e., selenium-containing protein) (Table 9). It is considered that the selenium-containing compound (chemical formula 1) according to one embodiment of the invention is involved in an in vivo antioxidant effect in the cells.

TABLE 7

HPLC-ICP-MS analysis conditions

| Element | Se |
| --- | --- |
| RF output (kW) | 1.5 |
| Nebulizer gas flow rate (Ar L/min) | 1 |
| Auxiliary gas flow rate (Ar L/min) | 1.3 |
| Plasma gas flow rate (Ar L/min) | 17 |
| Makeup gas flow rate | 0 |
| Lens voltage (V) | 8.2 |
| Reaction gas | None |
| Mass number (amu) | 82 |
| Pulse stage voltage | 1050 |
| RPq | 0.25 |
| HPLC conditions | |
| Column | Ultrahydrogel 120 (7.8 × 300 mm) |
| Mobile phase | 0.1M ammonium formate (pH: 7.0) |
| Flow rate | 1.0 ml/min |

TABLE 8

Selenium content in living tissues

| Species/tissue | Selenium-containing protein (nmol/g) | Selenium-containing compound (chemical formula 1) (nmol/g) | Ratio (%) of selenium-containing compounds other than selenium-containing compound (chemical formula 1) with respect to total selenium content |
| --- | --- | --- | --- |
| *Thunnus orientalis* dark muscle | 44.7 | 2018.9 | 2.5 |
| *Thunnus orientalis* ordinary muscle | 13.1 | 26.8 | 11.6 |
| *Thunnus orientalis* blood | 23.6 | 609 | 0.0 |
| Chicken heart | 20.2 | 1.1 | 44 |
| Chicken liver | 66.7 | 3.0 | 26 |
| Chicken gizzard | 26.8 | 0.0 | 39 |
| Pig liver | 80.0 | 0.0 | 38 |
| *Todarodes pacificus* hepatopancreas | 50.3 | 93.1 | 21 |

TABLE 9

Intracellular localization of novel selenium-containing compound

| Species/tissue Cell fraction | Selenium-containing protein (nmol/g) | Selenium-containing compound (chemical formula 1) (nmol/g) | Ratio (%) of selenium-containing compounds other than selenium-containing compound (chemical formula 1) with respect to total selenium content |
| --- | --- | --- | --- |
| *Thunnus orientalis* dark muscle | | | |
| Cytoplasmic fraction | 17.34 | 28.87 | 0.01 |
| Microsome fraction | 2.41 | 0.35 | 0.01 |
| Mitochondrial fraction | 0.40 | 0.20 | 0.02 |
| *Thunnus orientalis* ordinary muscle | | | |
| Cytoplasmic fraction | 0.71 | 1.04 | 0.00 |
| Microsome fraction | 0.11 | 0.16 | 0.02 |
| Mitochondrial fraction | 0.10 | 0.16 | 0.04 |

2. Chemical Antioxidant Ability of Selenium-Containing Compound

In order to evaluate the chemical antioxidant ability of the selenium-containing compound (chemical formula 4: oxidized dimer) according to one embodiment of the invention, the 1,1-diphenyl-2-picrylhydrazyl (DPPH) radical-scavenging ability was measured (Hideo Kimura, Kota Naganuma, Masato Kojima, Masakazu Komatsu, Takumi Onda, and Masao Tsuji, Yamanashi Prefectural Industrial Technology Center Report, No. 22, pp. 59-63 (2008)).

Specifically, a selenium-containing compound (selenium content: 1.62 µM) derived from the meat of *Xiphias gladius*, a 10 mM aqueous solution of a water-soluble vitamin E derivative (commercially available antioxidant) (Trolox (registered trademark) (CAS No.: 56305-04-5, manufactured by Roche)), and a 4.36 mM aqueous solution of (+)-ergothioneine (CAS No.: 497-30-3, manufactured by SIGMA) were repeatedly 2-fold diluted with purified water to prepare 2 to 128-fold diluted test solutions.

10 µl of the test solution and 100 µl of a DPPH solution (0.35 mM, prepared by dissolving 1.38 mg of DPPH in 5 ml of ethanol, and adding 5 ml of a 0.1 M phosphate buffer (pH: 6.8) to the solution) were mixed on a 96-well micro test plate (BD Falcon (registered trademark), #1722, manufactured by Becton, and Dickinson and Company), and reacted at room temperature for 30 minutes in a dark place. The absorbance at 595 nm was then measured. A case of using purified water (absorbance: 0.59) as the test solution was determined that the DPPH radical-scavenging rate was 0%, and a case of using 10 mM Trolox (registered trademark) (absorbance: 0.19) as the test solution was determined that the DPPH radical-scavenging rate was 100%. The concentration at which the DPPH radical-scavenging rate was 50% was determined to be the $RS_{50}$ of each substance, and taken as the antioxidant ability.

It was confirmed that the selenium-containing compound (chemical formula 4: oxidized dimer) according to one embodiment of the invention has a radical-scavenging ability equal to that of the water-soluble vitamin E derivative (Trolox (registered trademark)) at a concentration 1/456th of that of the water-soluble vitamin E derivative (Trolox (registered trademark)), and has a radical-scavenging ability equal to that of L-(+)-ergothioneine (sulfur-containing antioxidant) at a concentration 1/907th of that of L-(+)-ergothioneine. Specifically, it was confirmed that the selenium-containing compound (chemical formula 4: oxidized dimer) according to one embodiment of the invention has a very strong antioxidant ability.

TABLE 10

DPPH radical-scavenging ability of selenium-containing compound

| | $RS_{50}$ (µM) |
| --- | --- |
| Water-soluble vitamin E derivative (Trolox (registered trademark)) | 880 |
| L-(+)-ergothioneine | 1700 |
| Selenium-containing compound | 1.9 |

3. In Vivo Antioxidant Effect of Selenium-Containing Compound

In order to clarify the intracellular function of the selenium-containing compound (chemical formula 4: oxidized dimer) according to one embodiment of the invention, the selenium-containing compound (chemical formula 4: oxidized dimer) according to one embodiment of the invention was administered to human vessel endothelial cells (human umbilical cord vein HUV-EC-C, Health Science Research Resources Bank (http://www.jhsf.or.jp)).

Specifically, human vessel endothelial cells (10,000 cells/ml) were cultured on a 48-well plate using an MCDB131 medium (manufactured by Invitrogen) containing 10% fetal bovine serum. The selenium-containing compound was added to the culture solution so that the final concentration was 1, 2.5, 5, or 10 mM (control: the selenium-containing compound was not added), and the cells were cultured at 37°

C. for 24 hours under 5% carbon dioxide. The passage number was set to 5 or less in order to maintain the properties of the human vessel endothelial cells.

The mitochondrial respiratory chain activity was determined using an MTT assay kit (manufactured by Nacalai Tesque, Inc.). Specifically, after culturing the human vessel endothelial cells, an MTT solution was added to the culture solution in an amount 1/10th of that of the culture solution, and the cells were cultured at 37° C. for 3 hours under 5% carbon dioxide. An equal amount of isopropanol was then added to the culture solution to extract a formazan dye, and the absorbance at 595 nm was determined.

Figure 8:
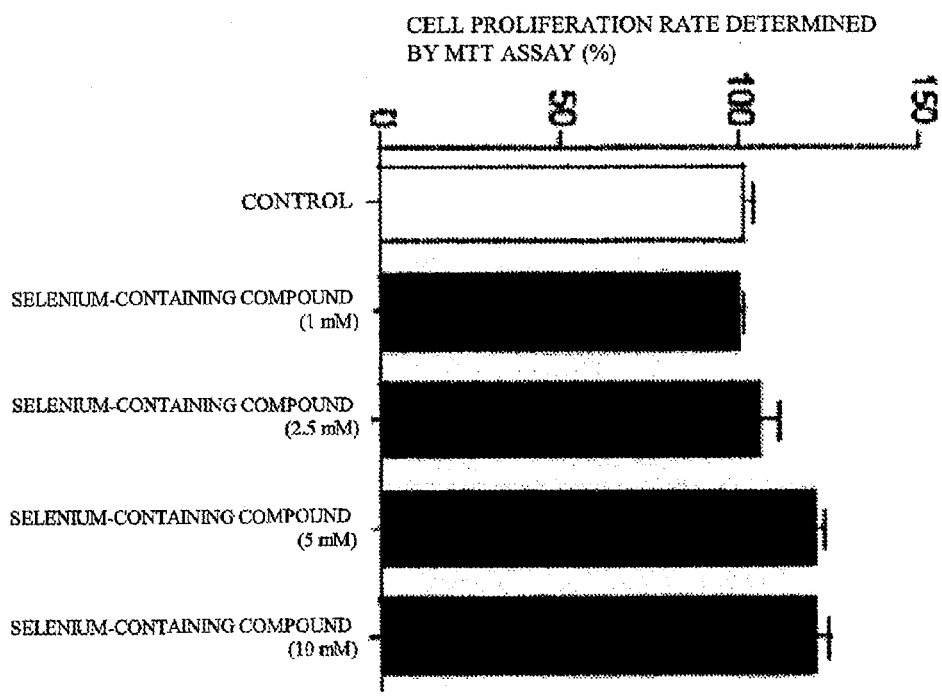
FIG. 8 is a view showing the in vivo antioxidant effect of a selenium-containing compound purified from the dark muscle using the cell proliferation rate (Example 5).
Figure 8:
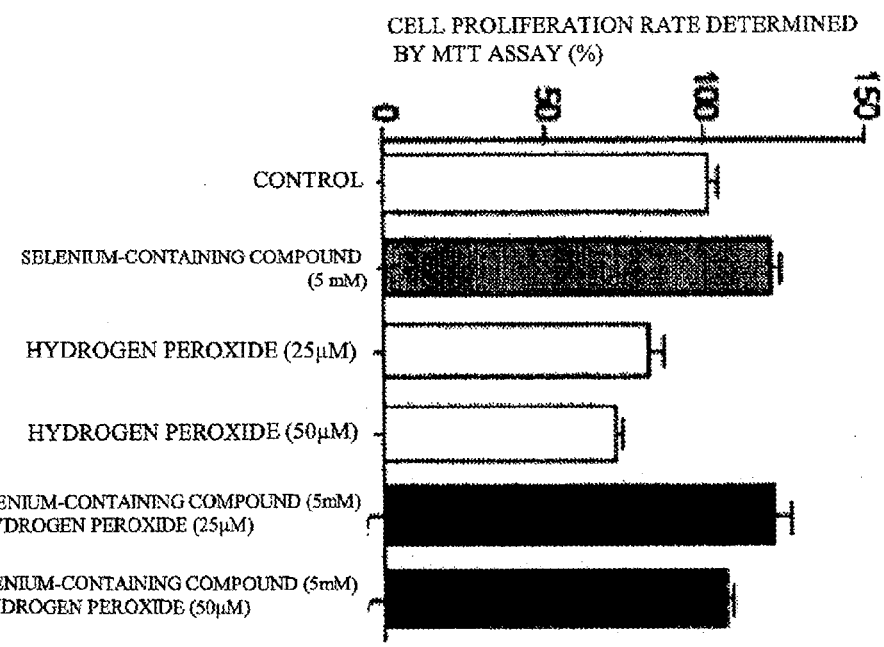

As shown in FIG. 8, the selenium-containing compound (chemical formula 4: oxidized dimer) according to one embodiment of the invention showed a cell proliferation-promoting effect at a concentration of 5 mM. When adding sodium selenite (manufactured by SIGMA), selenocystine (manufactured by SIGMA), or selenomethionine (manufactured by Tokyo Kasei Kogyo Co., Ltd.) to the culture medium of the human vessel endothelial cells to a concentration of 5 nM, cell death occurred instead of cell proliferation. It was thus confirmed that the selenium-containing compound (chemical formula 4: oxidized dimer) according to one embodiment of the invention has very low cytotoxicity as compared with known selenium-containing compounds such as selenious acid, selenocystine, and selenomethionine.

The in vivo antioxidant effect of the selenium-containing compound (chemical formula 4: oxidized dimer) according to one embodiment of the invention was determined using human vessel endothelial cells. Specifically, human vessel endothelial cells (10,000 cells/ml) were cultured on a 48-well plate using an MCDB131 medium containing 10% fetal bovine serum. The selenium-containing compound was added to the culture solution so that the final concentration was 5 mM (control: the selenium-containing compound was not added), and the cells were cultured at 37° C. for 1 hour under 5% carbon dioxide. After the addition of hydrogen peroxide to a final concentration of 25 or 50 µM, the cells were cultured at 37° C. for 24 hours under 5% carbon dioxide. The cell proliferation rate was then determined by the MTT assay. It was found that the cellular proliferative potential was improved under oxidative stress conditions due to hydrogen peroxide by adding the selenium-containing compound (chemical formula 4: oxidized dimer) according to one embodiment of the invention. Specifically, it was confirmed that the selenium-containing compound (chemical formula 4: oxidized dimer) according to one embodiment of the invention has an in vivo antioxidant effect.

It was thus confirmed that the selenium-containing compound (chemical formula 4: oxidized dimer) according to one embodiment of the invention added to a medium is incorporated in human cells, and exhibits an in vivo antioxidant effect on the cells. It is considered that the selenium-containing compound (chemical formula 4: oxidized dimer) according to one embodiment of the invention functions as a reducing agent in cytoplasm.

4. Cell Proliferation-Promoting Effect of Selenium-Containing Compound

The cell proliferation-promoting effect of the selenium-containing compound (chemical formula 4: oxidized dimer) according to one embodiment of the invention on cultured cells was determined.

Specifically, *Danio rerio* embryo ZE cells (National Research Institute of Fisheries Science), *Seriola quinqueradiata* tail fin YT cells (National Research Institute of Fisheries Science), and *Oncorhynchus mykiss* gonad RTG-2 cells (ATCCCCL55) were cultured in an L-15 medium containing 2% fetal bovine serum (30,000 cells/ml).

Human vessel endothelial cells (human umbilical cord vein HUV-EC-C, Health Science Research Resources Bank (http://www.jhsf.or.jp)) were cultured in an MCDB131 medium containing 10% fetal bovine serum (10,000 cells/ml).

AT cells derived from the skin of a human patient with ataxia telangiectasia syndrome (AT2KY, Health Science Research Resources Bank, JCRB0316), human skin TIG-S3 cells (Health Science Research Resources Bank, JCRB0544), and human kidney HEK293 cells (Health Science Research Resources Bank, JCRB9068) were cultured in a DMEM medium containing 10% fetal bovine serum (15,000 cells/ml).

The selenium-containing compound was added to each culture medium (containing 2% serum) so that the final concentration was 0, 5, 10, 25, 50, or 100 nM. The *Danio rerio* embryo ZE cells were cultured at 25° C., the *Seriola quinqueradiata* tail fin YT cells were cultured at 20° C., and *Oncorhynchus mykiss* gonad RTG-2 cells were cultured at 15° C., and the human vessel endothelial cells, the AT cells derived from the skin of a human patient with ataxia telangiectasia syndrome, the human skin TIG-S3 cells, and the human kidney HEK293 cells were cultured at 37° C. The cell count was determined by trypan blue staining after culturing the cells for 0, 1, 2, 3, 4, and 5 days.

Figure 9:
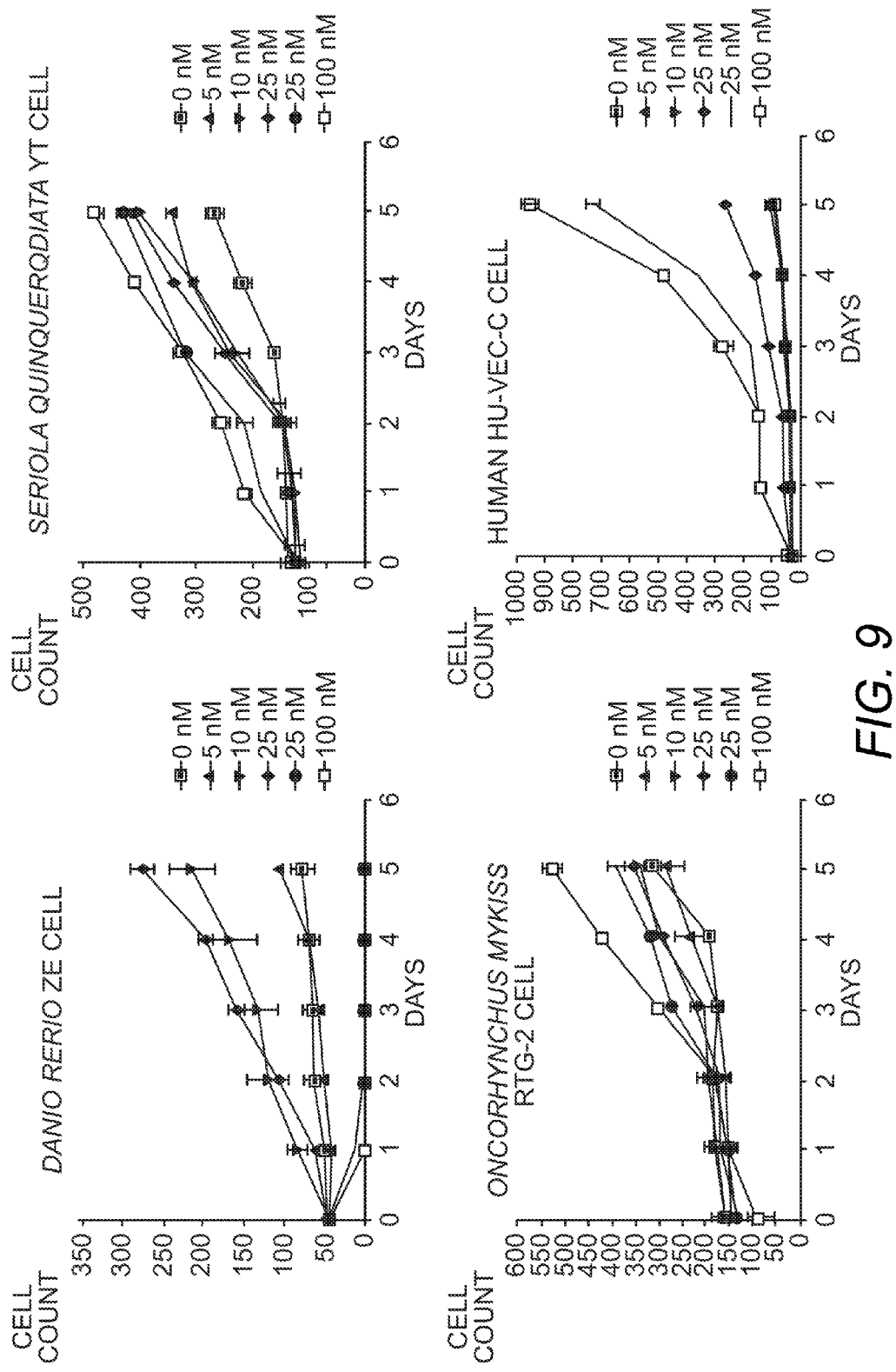
FIG. 9 is a view showing the cell proliferation-promoting effect of a selenium-containing compound (Example 5).
Figure 9:
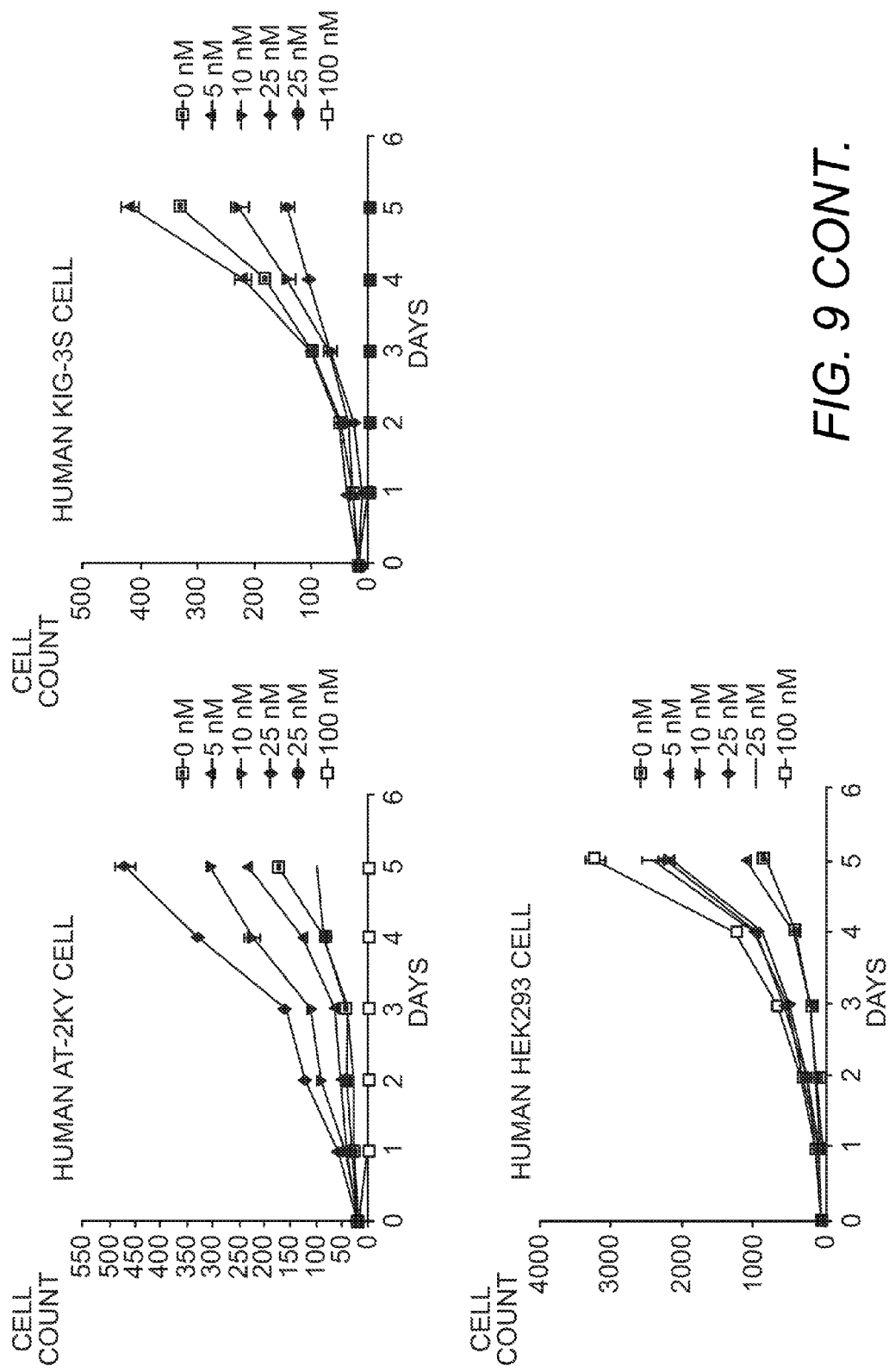

As shown in FIG. 9, it was confirmed that the concentration of the selenium containing compound necessary for promoting cell proliferation differs depending on the type of cell line. It was thus found that the selenium-containing compound significantly promotes proliferation of animal cells, and the amount of selenium-containing compound required to promote cell proliferation differs depending on the type of cells. It was thus confirmed that the selenium-containing compound can be used as a medium additive when culturing animal cells.

Since the AT cells derived from the skin of a human patient with ataxia telangiectasia syndrome lack an ATM kinase gene that is an uppermost stream signalling factor that responds to DNA damage, aging and cancer are induced by abnormalities in DNA repair and apoptosis (K. Naka, A. Tachibana, K. Ikeda, and N. Motoyama, J. Biol. Chem., 279, pp. 2030-2037 (2004)). Since the selenium-containing compound (chemical formula 4: oxidized dimer) according to one embodiment of the invention had an effect of promoting proliferation of the AT cells, it is considered that the selenium-containing compound has an in vivo antioxidant effect that recovers the DNA damage response.

5. Metmyoglobin Formation Inhibitory Effect of Selenium-Containing Compound

Preserved rabbit blood (Nippon Biotest Laboratories Inc.) was washed three times with a physiological saline solution (centrifuged at 2000 rpm and 4° C. for 5 min) to collect red cells. The red cells were suspended in a 4-fold amount of an RPMI medium (GIBCO (registered trademark) RPMI Medium 1640 manufactured by Invitrogen Co.), and cultured at 37° C. for 1 day using a carbon dioxide incubator. The selenium-containing compound was added to the culture solution so that the final concentration of the selenium-containing compound in the medium was 10, 25, or 50 nM (control: the selenium-containing compound was not added), and the cells were cultured. The red cells were then collected by centrifugation (2000×g, 4° C., 5 min), washed three times with a phosphate buffered saline (PBS), and collected by centrifugation. The red cells were hemolyzed by adding a 10 mM sodium phosphate buffer (pH: 7.2) to the red cell pellets, and centrifuged (15,000×g, 4° C., 10 min). The supernatant hemoglobin solution was then collected. The hemoglobin solution was diluted with a 100-fold amount of a 50 mM sodium phosphate buffer (pH: 6.8), and incubated at 37° C. for 3 hours. The absorbance ratio at 405 nm and 430 nm before and after incubation was measured, and the rate of metmyoglobin formation of the hemoglobin was calculated.

The active oxygen level in the red cells was also measured using hydroxyphenyl fluorescein (HPF) (manufactured by Sekisui Medical Co., Ltd.). The hemoglobin solution was mixed with a 100-fold amount of HPF diluted with a 1000-fold amount of a phosphate buffered saline (PBS), and reacted at room temperature for 10 minutes. The fluorescence intensity (excitation wavelength: 490 nm, fluorescence wavelength: 515 nm) due to the reaction product with active oxygen was measured, and used as an index of the active oxygen level.

Figure 10:
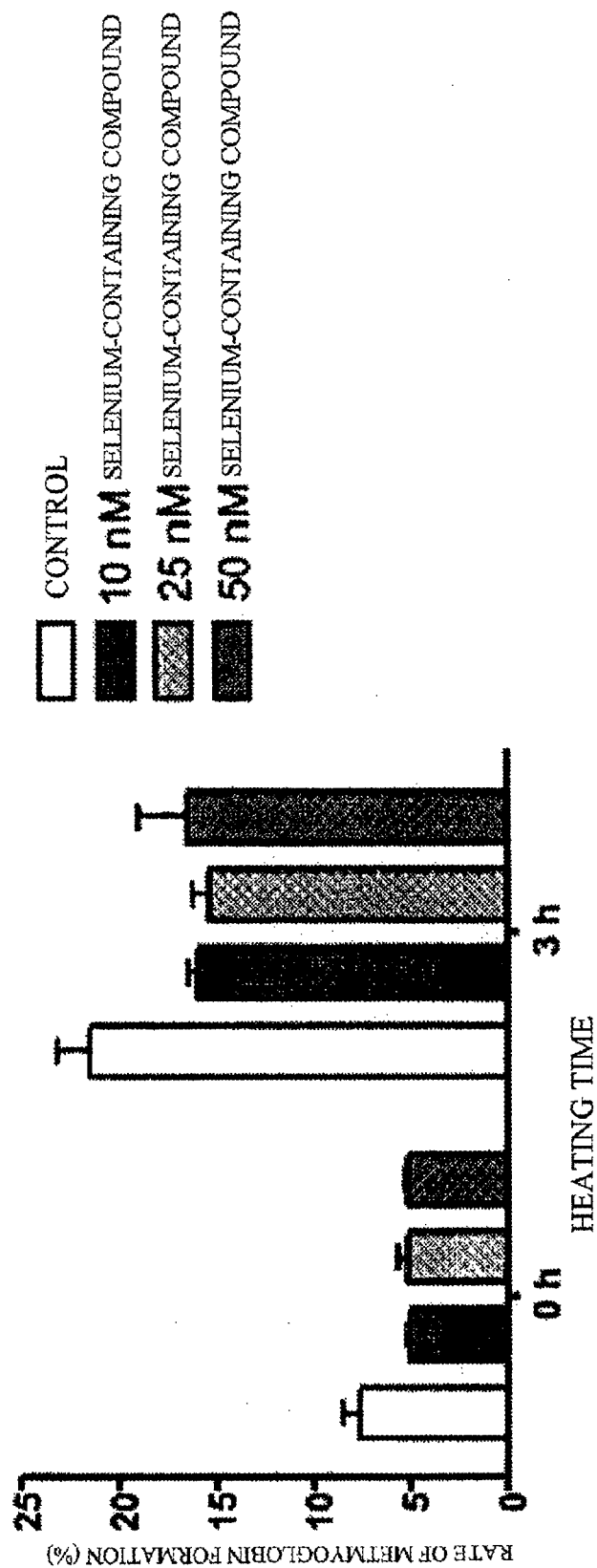
FIG. 10 is a view showing the rate of metmyoglobin formation of hemoglobin collected from red cells (Example 5).
Figure 11:
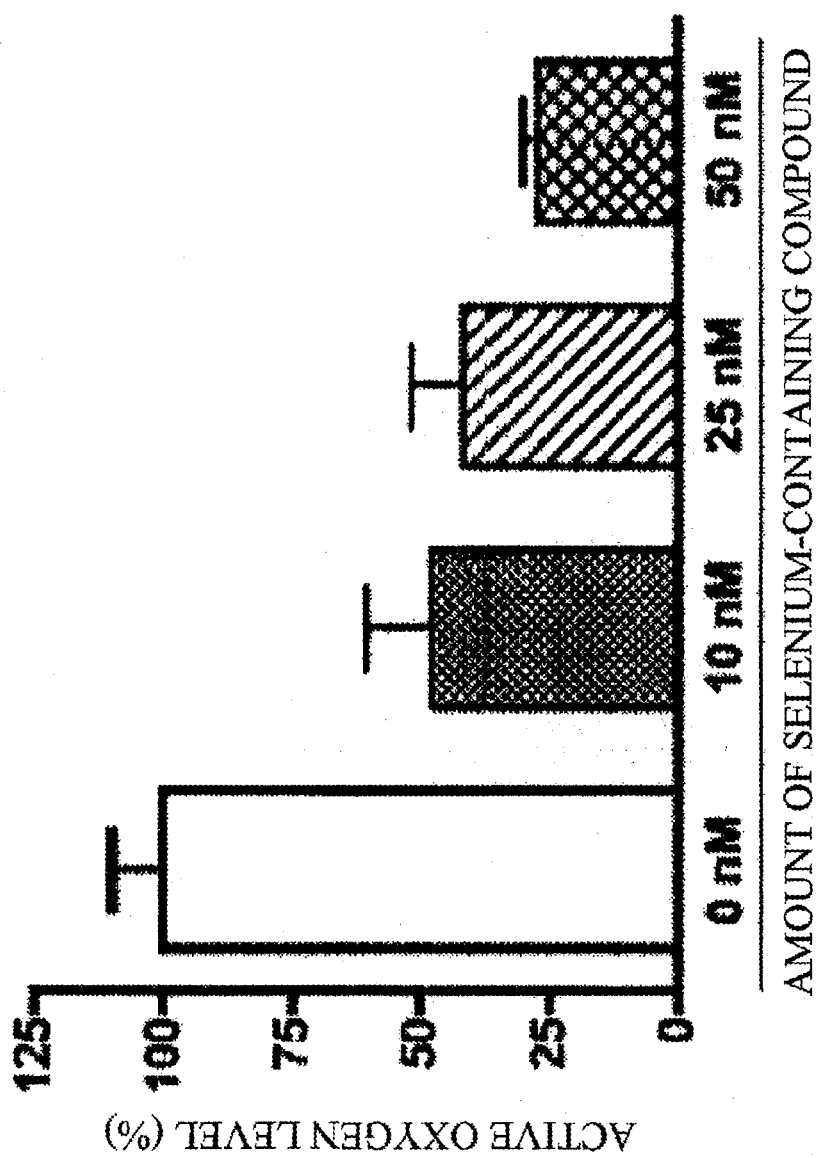
FIG. 11 is a view showing the active oxygen level in a hemoglobin solution collected from red cells (Example 5).

As shown in FIG. 10, the rate of metmyoglobin formation of the red cells at each concentration of the selenium-containing compound was lower than that of the control. As shown in FIG. 11, the active oxygen level in the red cells achieved when adding the selenium-containing compound was lower than that of the control. It was thus confirmed that the selenium-containing compound has an in vivo antioxidant effect that suppresses in vivo methemoprotein formation. Specifically, it was confirmed that the selenium-containing compound is incorporated in cells from a medium, prevents production of active oxygen, and functions as a heme iron auto-oxidation inhibitor. It was thus confirmed that the selenium-containing compound may be used for blood/red cell/internal organ preservation technology (i.e., may be used as a metmyoglobin formation inhibitor for heme proteins (e.g., hemoglobin and myoglobin), artificial blood, transfusion preparations, or tissue preservation solutions).

6. Heme Iron Binding Effect of Selenium-Containing Compound

Since it was confirmed that the selenium-containing compound has a heme protein auto-oxidation inhibitory effect (see "5. Metmyoglobin formation inhibitory effect of selenium-containing compound"), the binding capability of the selenium-containing compound with heme proteins was determined. *Physeter macrocephalus* (sperm whale) myoglobin available from SIGMA was used. 100 g of the dark muscle of *Thunnus orientalis* was mixed with a 5-fold amount of cold water, ground using a POLYTRON™ homogenizer, and centrifuged (6000×g, 10 min). The supernatant liquid was collected, and passed through a Sephacryl-100 column (16 mm×60 cm, manufactured by Pharmacia) that was equilibrated with a 0.05 M Tris-HCl buffer (pH: 7) containing 0.1 M salt to purify myoglobin derived from the dark muscle of *Thunnus orientalis*. Hemoglobin was obtained by purifying a lysate of the red cells of rabbit or *Thunnus orientalis* using the Sephacryl-100 column.

The selenium content in the *Physeter macrocephalus* myoglobin, the *Thunnus orientalis* myoglobin, the rabbit hemoglobin, and the *Thunnus orientalis* hemoglobin was measured. Selenium was detected from each sample. The elements contained in the *Physeter macrocephalus* myoglobin were measured by HPLC-ICP-MS. As shown in FIG. 12, iron and selenium were detected from the *Physeter macrocephalus* myoglobin.

The sample was wet-decomposed using nitric acid and hydrogen peroxide. Iron was quantitatively determined using an inductively coupled plasma atomic emission spectrometer (ICP-AES) ("ICPE-9000" manufactured by Shimadzu Corporation), and selenium was quantitatively determined by fluorometry. The Se/Fe molar ratio of the *Thunnus orientalis* myoglobin, the rabbit hemoglobin, and the *Thunnus orientalis* hemoglobin was 0.003, 0.0003, and 0.001, respectively. It was thus confirmed that the selenium-containing compound (chemical formula 4: oxidized dimer) according to one embodiment of the invention was bound to a heme protein. It is considered that the selenium-containing compound is coordinated to heme iron to suppress auto-oxidation of heme iron.

Since the selenium-containing compound according to one embodiment of the invention has an in vivo antioxidant effect, the selenium-containing compound may be used for, or as, a drug, a functional food, a nutritional supplement, a food additive, a feed additive, a medium additive, or an antioxidant. It is also possible to provide a method of producing a safe selenium-containing compound by removing heavy metals from fishery processing residues (e.g., dark muscle, internal organs, and blood). The chemical form of selenium in a living body, food, and the like can be evaluated by utilizing the selenium-containing compound according to one embodiment of the invention as a standard substance. Since the selenium-containing compound according to one embodiment of the invention includes a selenol group having high reactivity, and has fluorescent and UV absorption characteristics, the selenium-containing compound may be used as unique selenium-containing chemical materials (e.g., chemical modifier, fluorescent substance, or UV absorber).

What is claimed is:

1. A method of analyzing a selenium-containing compound in a sample, which comprises analyzing a selenium-containing compound in the sample using, as a standard substance, an isolated or purified selenium-containing compound shown by the following chemical formula 1:

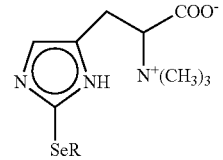

Chemical formula 1 wherein R is absent, or represents hydrogen or an organic compound, and wherein the method comprises the following steps:

(1) separating selenium-containing compound(s) contained in the sample by a chromatography to obtain a chromatogram for the selenium-containing compound(s) contained in the sample, and (2) comparing the obtained chromatogram with a corresponding chromatogram for the isolated or purified selenium-containing compound shown by the chemical formula 1.

2. The method of claim 1, wherein the selenium-containing compound is chosen from the following chemical formulas:

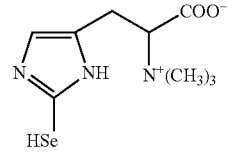

Chemical formula 2

3-(2-hydroseleno-1H-imidazol-5-yl)-
2-(trimethylammonio)propanoate

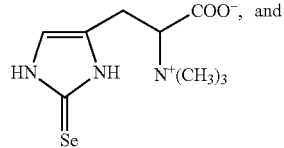

Chemical formula 3

3-(2-selenoxo-2,3-dihydro-1H-imidazol-4-yl)-
2-(trimethylammonio)propanoate

Chemical formula 4

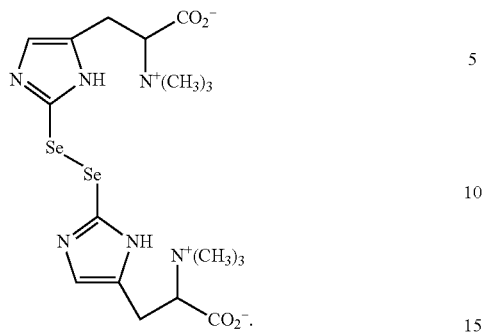

3,3'-(2,2'-diselanediylbis(1H-imidazole-5,2-diyl))bis(2-(trimethylammonio)propanoate)

3. The method of claim 1, wherein the sample is derived from a living body or a food.

4. The method of claim 1, wherein the chromatography is a gel-filtration chromatography.

5. The method of claim 1, wherein ICP-MS is used in combination with the chromatography.

6. The method of claim 4, wherein ICP-MS is used in combination with the gel-filtration chromatography.

* * * * *